US012611455B2

(12) United States Patent
Shih et al.

(10) Patent No.: US 12,611,455 B2
(45) Date of Patent: Apr. 28, 2026

(54) DNA NANOSTRUCTURE-BASED VACCINES

(71) Applicants: Dana-Farber Cancer Institute, Inc., Boston, MA (US); Korea Institute of Science and Technology, Seoul (KR)

(72) Inventors: William M. Shih, Cambridge, MA (US); Ju Hee Ryu, Brookline, MA (US); Yang Zeng, Winchester, MA (US)

(73) Assignees: Dana-Farber Cancer Institute, Inc., Boston, MA (US); Korea Institute of Science and Technology, Seoul (KR)

( * ) Notice: Subject to any disclaimer, the term of this patent is extended or adjusted under 35 U.S.C. 154(b) by 1048 days.

(21) Appl. No.: 17/616,971

(22) PCT Filed: Jun. 5, 2020

(86) PCT No.: PCT/US2020/036281

§ 371 (c)(1),
(2) Date: Dec. 6, 2021

(87) PCT Pub. No.: WO2020/247724

PCT Pub. Date: Dec. 10, 2020

(65) Prior Publication Data

US 2022/0305119 A1     Sep. 29, 2022

Related U.S. Application Data

(60) Provisional application No. 62/858,783, filed on Jun. 7, 2019.

(51) Int. Cl.

| | |
|---|---|
| *A61K 39/39* | (2006.01) |
| *A61K 9/00* | (2006.01) |
| *A61K 9/06* | (2006.01) |
| *A61K 39/00* | (2006.01) |
| *A61K 47/54* | (2017.01) |
| *A61K 47/60* | (2017.01) |
| *A61K 47/64* | (2017.01) |
| *B82Y 5/00* | (2011.01) |

(52) U.S. Cl.
CPC ............ *A61K 39/39* (2013.01); *A61K 9/0019* (2013.01); *A61K 9/0053* (2013.01); *A61K 9/06* (2013.01); *A61K 47/549* (2017.08); *A61K 47/60* (2017.08); *A61K 47/645* (2017.08)

(58) Field of Classification Search
None
See application file for complete search history.

(56) References Cited

U.S. PATENT DOCUMENTS

| | | | |
|---|---|---|---|
| 7,842,793 B2 | 11/2010 | Rothemund | |
| 8,501,923 B2 | 8/2013 | Rothemund | |
| 9,717,685 B2 | 8/2017 | Shih et al. | |
| 2005/0112578 A1 | 5/2005 | Matsuura et al. | |
| 2006/0105049 A1 | 5/2006 | Fernandes et al. | |
| 2009/0088372 A1 | 4/2009 | Roy et al. | |
| 2010/0216978 A1 | 8/2010 | Shih | |
| 2010/0324124 A1 | 12/2010 | Irvine et al. | |
| 2011/0275702 A1 | 11/2011 | Chang et al. | |
| 2011/0321183 A1 | 12/2011 | Ploegh et al. | |
| 2012/0282670 A1 | 11/2012 | Rossomando | |
| 2013/0230570 A1 | 9/2013 | Trogler et al. | |
| 2015/0064233 A1 | 3/2015 | Shih et al. | |
| 2016/0271268 A1* | 9/2016 | Shih .................... A61K 47/645 |
| 2016/0279257 A1 | 9/2016 | Koussa et al. | |
| 2019/0083522 A1 | 3/2019 | Shih et al. | |

FOREIGN PATENT DOCUMENTS

| | | | |
|---|---|---|---|
| EP | 2275085 A1 | 1/2011 | |
| JP | 2002-114797 A | 4/2002 | |
| JP | 2003-522524 A | 7/2003 | |
| JP | 2008-504846 A | 2/2008 | |
| JP | 2008-523061 A | 7/2008 | |
| JP | 2009-518008 A | 5/2009 | |
| JP | 2009-213390 A | 9/2009 | |
| JP | 2012-509983 A | 4/2012 | |
| WO | 2001/18015 A1 | 3/2001 | |
| WO | WO 2012/142659 A1 | 10/2012 | |
| WO | WO 2013/003555 A1 | 1/2013 | |
| WO | WO 2013/054286 A1 | 4/2013 | |
| WO | WO 2013/113325 A1 | 8/2013 | |
| WO | WO 2013/148186 A1 | 10/2013 | |
| WO | WO-2017189870 A1 * | 11/2017 | ............ G16B 15/10 |

OTHER PUBLICATIONS

Ke, Yonggang, et al. "Multilayer DNA origami packed on a square lattice." Journal of the American Chemical Society 131.43 (2009): 15903-15908. DOI: 10.1021/ja906381y (Year: 2009).*
Ponnuswamy, N., Bastings, M., Nathwani, B. et al. Oligolysine-based coating protects DNA nanostructures from low-salt denaturation and nuclease degradation. Nat Commun 8, 15654 (2017). https://doi.org/10.1038/ncomms15654 (Year: 2017).*
Li, Jiang, et al. "Self-assembled multivalent DNA nanostructures for noninvasive intracellular delivery of immunostimulatory CpG oligonucleotides." ACS nano 5.11 (2011): 8783-8789. (Year: 2011).*
Schuller, Verena J., et al. "Cellular immunostimulation by CpG-sequence-coated DNA origami structures." ACS nano 5.12 (2011): 9696-9702. (Year: 2011).*
PCT/US2020/036281, Sep. 30, 2020, International Search Report and Written Opinion.

(Continued)

*Primary Examiner* — Bethany P Barham
*Assistant Examiner* — Peter Anthopolos
(74) *Attorney, Agent, or Firm* — Wolf, Greenfield & Sacks, P.C.

(57) ABSTRACT

Provided herein, in some embodiments, are nucleic acid nanostructure-based vaccines.

19 Claims, 20 Drawing Sheets

Specification includes a Sequence Listing.

(56)　　　　　References Cited

OTHER PUBLICATIONS

PCT/US2020/036281, Dec. 16, 2021, International Preliminary Report on Patentability.

International Search Report and Written Opinion mailed Sep. 30, 2020 for Application No. PCT/US2020/036281.

International Preliminary Report on Patentability mailed Dec. 16, 2021 for Application No. PCT/US2020/036281.

Babic et al. Poly L-lysine-modified iron oxide nanoparticle for stem cell labelling. Bioconjug Chem. 2008;19:740-50. Epub Feb. 21, 2008.

Banchelli et al., Phospholipid membranes decorated by cholesterol-based oligonucleotides as soft hybrid nanostructures. J Phys Chem B. Sep. 4, 2008;112(35):10942-52.

Bellot et al., Recovery of intact DNA nanostructures after agarose gel-based separation. Nat Methods. Mar. 2011;8(3):192-4.

Bikram et al., Biodegradable Poly(ethylene glycol)-co-poly(l-lysine)-g-histidine Multiblock Copolymers for Nonviral Gene Delivery. Macromolecules. Feb. 11, 2004;37(5):1903-16.

Cecconi et al., Protein-DNA chimeras for single molecule mechanical folding studies with the optical tweezers. Eur Biophys J. Jul. 2008;37(6):729-38. doi: 10.1007/s00249-007-0247-y. Epub Jan. 9, 2008.

Chen et al., A general strategy for the evolution of bond-forming enzymes using yeast display.Proc Natl Acad Sci U S A. Jul. 12, 2011;108(28):11399-404. doi: 10.1073/pnas.1101046108. Epub Jun. 22, 2011.

Davis et al., Preparation and analysis of PEGylated poly-L-lysine DNA nanoparticles for gene delivery. Cold Spring Harb Protoc. May 2010;2010(5):pdb.prot5419. doi: 10.1101/pdb.prot5419.

Dietz et al., Folding DNA into twisted and curved nanoscale shapes. Science. Aug. 7, 2009;325(5941):725-30.

Douglas et al., Rapid prototyping of 3D DNA-origami shapes with caDNAno. Nucleic Acids Res. Aug. 2009;37(15):5001-6.

Douglas et al., Self-assembly of DNA into nanoscale three-dimensional shapes. Nature. May 21, 2009;459(7245):414-8. Author Manuscript, 11 pages.

Eskelinen et al., Controlling the formation of DNA origami structures with external signals. Small. Jul. 9, 2012;8(13):2016-20. doi: 10.1002/smll.201102697. Epub Apr. 17, 2012.

Evett et al., DNA-polylysine interaction as studied by polarization of fluorescence. Ann N Y Acad Sci. May 16, 1969;158(1):210-22.

Fujigaya et al., Enhanced cell uptake via non-covalent decollation of a single-walled carbon nanotube-DNA hybrid with polyethylene glycol-grafted poly(l-lysine) labeled with an Alexa-dye and its efficient uptake in a cancer cell. Nanoscale. Oct. 5, 2011;3(10):4352-8. doi: 10.1039/c1nr10635j. Epub Sep. 20, 2011.

Gordon et al., Reactivity of biarylazacyclooctynones in copper-free click chemistry. J Am Chem Soc. Jun. 6, 2012;134(22):9199-208. doi: 10.1021/ja3000936. Epub May 24, 2012.

Halvorsen et al., Nanoengineering a single-molecule mechanical switch using DNA self-assembly. Nanotechnology. Dec. 9, 2011;22(49):494005. doi: 10.1088/0957-4484/22/49/494005. Epub Nov. 21, 2011.

Han et al., DNA origami with complex curvatures in three-dimensional space. Science. Apr. 15, 2011;332(6027):342-6. doi: 10.1126/science.1202998.

Högberg et al., Folding DNA origami from a double-stranded source of scaffold. J Am Chem Soc. Jul. 8, 2009;131(26):9154-5. doi: 10.1021/ja902569x.

Hook et al., Supported lipid bilayers, tethered lipid vesicles, and vesicle fusion investigated using gravimetric, plasmonic, and micros-copy techniques. Biointerphases. Jun. 2008;3(2):FA108.

Howarth et al., A monovalent streptavidin with a single femtomolar biotin binding site. Nat Methods. Apr. 2006;3(4):267-73.

Jones et al., Nanomaterials. Programmable materials and the nature of the DNA bond. Science. Feb. 20, 2015;347(6224):1260901. doi:10.1126/science.1260901.

Jungmann et al., Isothermal assembly of DNA origami structures using denaturing agents. J Am Chem Soc. Aug. 6, 2008;130(31):10062-3.

Kadlecova et al., DNA delivery with hyperbranched polylysine: a comparative study with linear and dendritic polylysine. J Control Release. Aug. 10, 2013;169(3):276-88. doi: 10.1016/j.jconrel.2013.01.019. Epub Feb. 1, 2013.

Kadlecova et al., Hyperbranched polylysine: a versatile, biodegradable transfection agent for the production of recombinant proteins by transient gene expression and the transfection of primary cells. Macromol Biosci. Jun. 2012;12(6):794-804. doi: 10.1002/mabi.201100519. Epub Apr. 11, 2012.

Kazmierczak et al., Cadherin 23 and protocadherin 15 interact to form tip-link filaments in sensory hair cells. Nature. Sep. 6, 2007;449(7158):87-91.

Ke et al., Multilayer DNA origami packed on a square lattice. J Am Chem Soc. Nov. 4, 2009;131(43):15903-8. doi: 10.1021/ja906381y.

Ko et al., Self-assembling micelle-like nanoparticles based on phospholipid-polyethyleneimine conjugates for systemic gene delivery. J Control Release. Jan. 19, 2009;133(2):132-8.

Kwoh et al., Stablilization of poly-L-lysine/DNA polyplexes for in vivo gene delivery to the liver. Biochimica et Biophysica Acta. 1999;1444:171-90.

Langecker et al., Synthetic lipid membrane channels formed by designed DNA nanostructures. Science. Nov. 16, 2012;338(6109):932-6. doi: 10.1126/science.1225624.

Lee et al., A review of immune amplification via ligand clustering by self-assembled liquid-crystalline DNA complexes. Adv Colloid Interface Sci. Jun. 2016;232:17-24. Epub Feb. 19, 2016.

Leleux et al., Biophysical attributes of CpG presentation control TLR9 signaling to differentially polarize systemic immune responses. Cell Rep. Jan. 17, 2017;18(3):700-710.

Li et al., Self-assembled multivalent DNA nanostructures for non-invasive intracellular delivery of immunostimulatory CpG oligo-nucleotides. ACS Nano. Nov. 22, 2011;5(11):8783-9. Epub Oct. 17, 2011.

Liedl et al., Self-assembly of three-dimensional prestressed tensegrity structures from DNA. Nat Nanotechnol. Jul. 2010;5(7):520-4. doi: 10.1038/nnano.2010.107. Epub Jun. 20, 2010.

Linko et al., The enabled state of DNA nanotechnology. Curr Opin Biotechnol. Aug. 2013;24(4):555-61. doi: 10.1016/j.copbio.2013.02.001. Epub Apr. 6, 2013.

Liu et al., A DNA nanostructure platform for directed assembly of synthetic vaccines. Nano Lett. Aug. 8, 2012;12(8):4254-9. Epub Jul. 6, 2012.

Liu et al., Biological properties of poly-L-lysine-DNA complexes generated by cooperative binding of the polycation. J Biol Chem. Sep. 14, 2001;276(37):34379-87. Epub Jul. 3, 2001.

Mann et al., DNA condensation by poly-L-lysine at the single molecule level: role of DNA concentration and polymer length. J Control Release. Feb. 11, 2008;125(3):252-62. Epub Nov. 1, 2007.

Martin, Functional Synthetic DNA Nanostructures. Dissertation. Technische Universität München, Laboratory for Biomolecular Nanotechnology. Filed on Mar. 12, 2013.

Maruyama et al., Characterization of interpolyelectrolyte complexes between double-stranded DNA and polylysine comb-type copolymers having hydrophilic side chains. Bioconjugate Chem. 1998;9:292-9. Epub Feb. 24, 1998.

Molas et al., Single-stranded DNA condensed with poly-L-lysine results in nanometric particles that are significantly smaller, more stable in physiological ionic strength fluids and afford higher efficiency of gene delivery than their double-stranded counterparts. Biochim Biophys Acta. Aug. 15, 2002;1572(1):37-44.

Niemeyer, The developments of semisynthetic DNA-protein conjugates. Trends Biotechnol. Sep. 2002;20(9):395-401.

Nikolov et al., Behavior of giant vesicles with anchored DNA molecules. Biophys J. Jun. 15, 2007;92(12):4356-68.

Pinheiro et al., Challenges and opportunities for structural DNA nanotechnology. Nat Nanotechnol. Nov. 6, 2011;6(12):763-72.

Ponnuswamy et al., Oligolysine-based coating protects DNA nanostructures from low-salt denaturation and nuclease degradation. Nat Commun. May 31, 2017;8:15654(1-9).

(56)        References Cited

OTHER PUBLICATIONS

Ponnuswamy, Polymine induced stability of DNA nanostructures against Mg depletion and nuclease activity. Presentation. Dana Farber Institute. Wyss Institute. Oct. 17, 2013.

Popp et al., Sortagging: a versatile method for protein labeling.Nat Chem Biol. Nov. 2007;3(11):707-8. Epub Sep. 23, 2007.

Rothemund, Folding DNA to create nanoscale shapes and patterns. Nature. Mar. 16, 2006;440(7082):297-302.

Saccà et al., Functionalization of DNA nanostructures with proteins. Chem Soc Rev. Dec. 2011;40(12):5910-21. doi: 10.1039/c1cs15212b. Epub Oct. 5, 2011.

Schaeffer et al., Synthesis and applications of covalent protein-DNA conjugates. Aust J Chem. Jan. 1, 2009;62(10):1328-1332.

Scheiermann et al., Clinical evaluation of CpG oligonucleotides as adjuvants for vaccines targeting infectious diseases and cancer. Vaccine. Nov. 12, 2014;32(48):6377-89. Epub Jun. 24, 2014.

Schmidt et al., Liquid-crystalline ordering of antimicrobial peptide-DNA complexes controls TLR9 activation. Nat Mater. Jul. 2015;14(7):696-700. Epub Jun. 8, 2015.

Schüller et al., Cellular immunostimulation by CpG-sequence-coated DNA origami structures. ACS Nano. Dec. 27, 2011;5(12):9696-702. Epub Nov. 23, 2011.

Shih et al., A 1.7-kilobase single-stranded DNA that folds into a nanoscale octahedron. Nature. Feb. 12, 2004;427(6975):618-21.

Shih et al., Biomolecular assembly: dynamic DNA. Nat Mater. Feb. 2008;7(2):98-100.

Shih et al., Knitting complex weaves with DNA origami. Curr Opin Struct Biol. Jun. 2010;20(3):276-82. Epub Apr. 22, 2010.

Shih et al., poster. DNA-Based Molecular Containers and NMR Alignment Media. 2006. 1 page.

Sotomayor et al., Structural determinants of cadherin-23 function in hearing and deafness. Neuron. Apr. 15, 2010;66(1):85-100. doi: 10.1016/j.neuron.2010.03.028.

Sotomayor et al., Structure of a force-conveying cadherin bond essential for inner-ear mechanotransduction. Nature. Dec. 6, 2012;492(7427):128-32. doi: 10.1038/nature11590. Epub Nov. 7, 2012.

Walsh et al., DNA cage delivery to mammalian cells. ACS Nano. 2011;5(7):5427-32. Epub Jun. 22, 2011. Supplemental information, 12 pages.

Yang et al., Nanostructures as Programmable Biomolecular Scaffolds. Bioconjug Chem. Aug. 19, 2015;26(8):1381-95. doi:10.1021/acs.bioconjchem.5b00194. Epub May 22, 2015.

Yoshina-Ishii et al., General method for modification of liposomes for encoded assembly on supported bilayers. J Am Chem Soc. Feb. 9, 2005;127(5):1356-7.

Zama et al., The study of the DNA structure in DNA-polylysine and DNA-polyarginine complexes: induced optical activities of bound dyes.Biochim Biophys Acta. Jan. 19, 1973;294(1):214-26.

Zhang et al., Structural DNA nanotechnology: state of the art and future perspective. J Am Chem Soc. Aug. 13, 2014;136(32):11198-211. doi:10.1021/ja505101a. Epub Jul. 28, 2014.

Zhou et al., Lipophilic polylysines mediate efficient DNA transfection in mammalian cells. Biochim Biophys Acta. May 31, 1991;1065(1):8-14.

Zhu et al. Hollow mesoporous silica poly-(l-lysine) particles for codelivery of drug and gene with enzyme-triggered release property. J Phys Chem C. Jun. 2011;115:13630-5. Epub Jun. 15, 2011.

Zhu et al., A novel nonviral nanoparticle gene vector: Poly-L-lysine-silica nanoparticles. Chinese Science Bulletin. Apr. 2002, 47(8): 654-658.

* cited by examiner

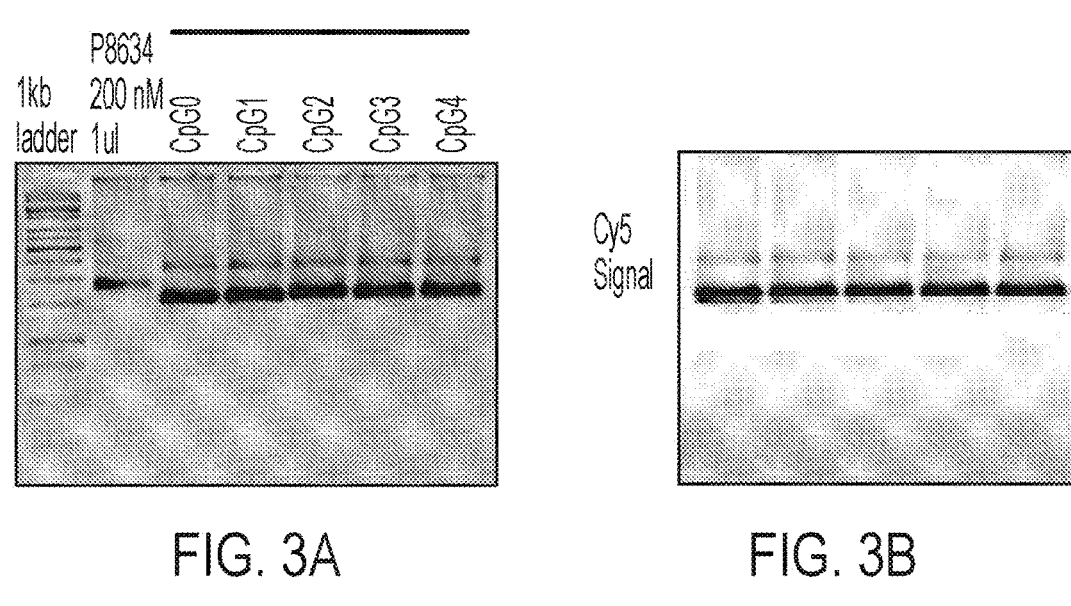
FIG. 3A                          FIG. 3B
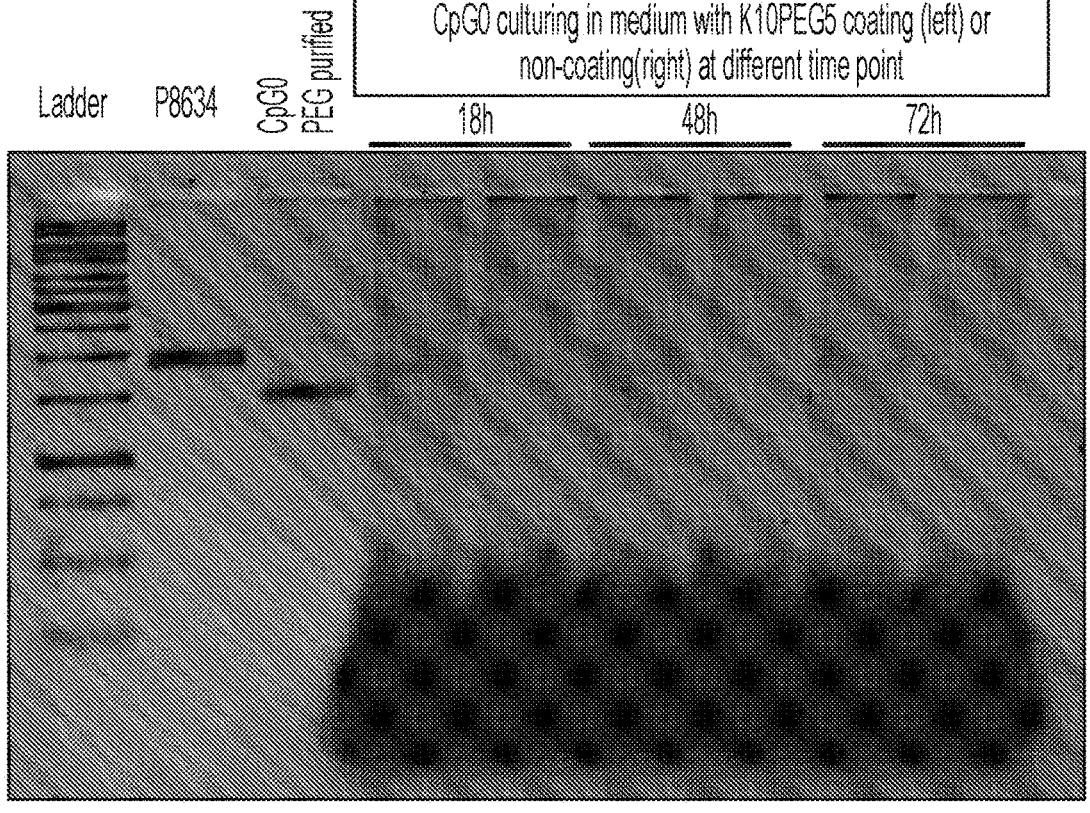
FIG. 3C

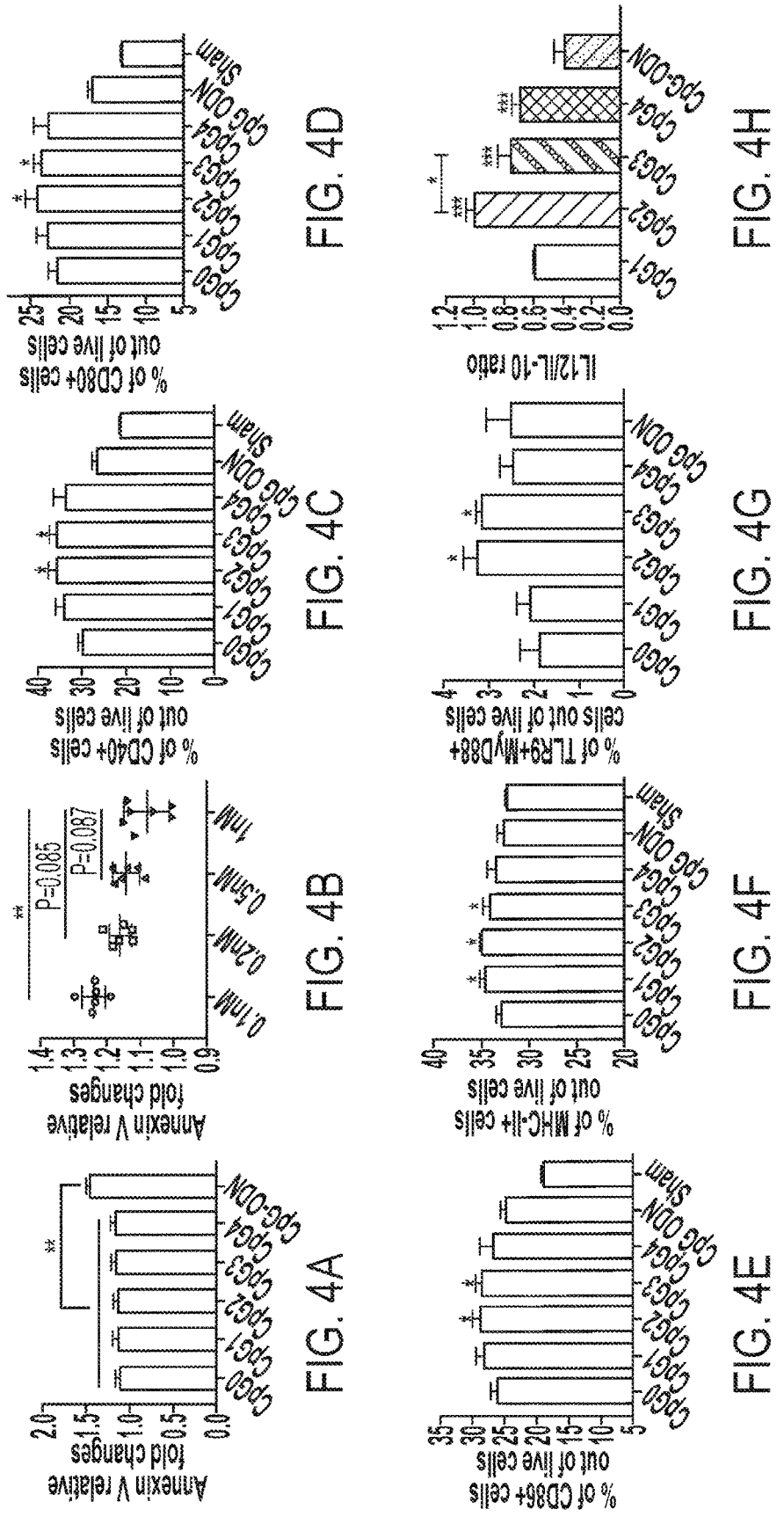

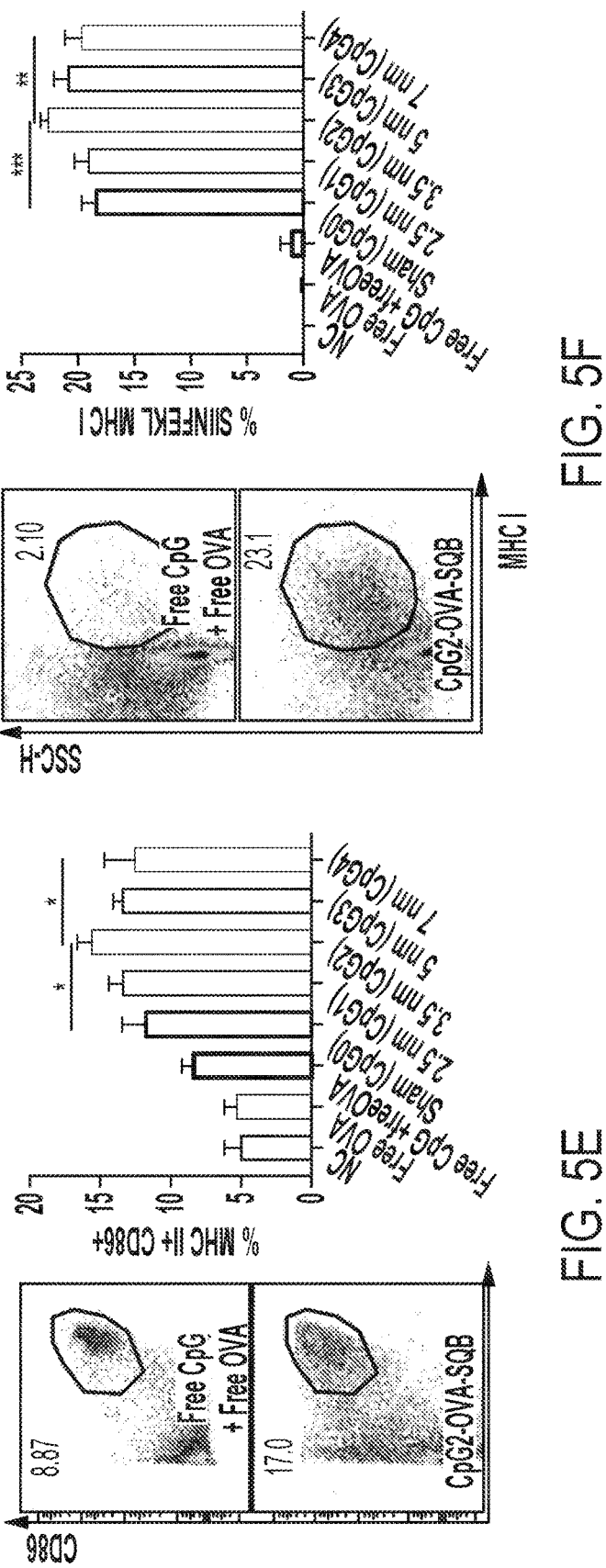

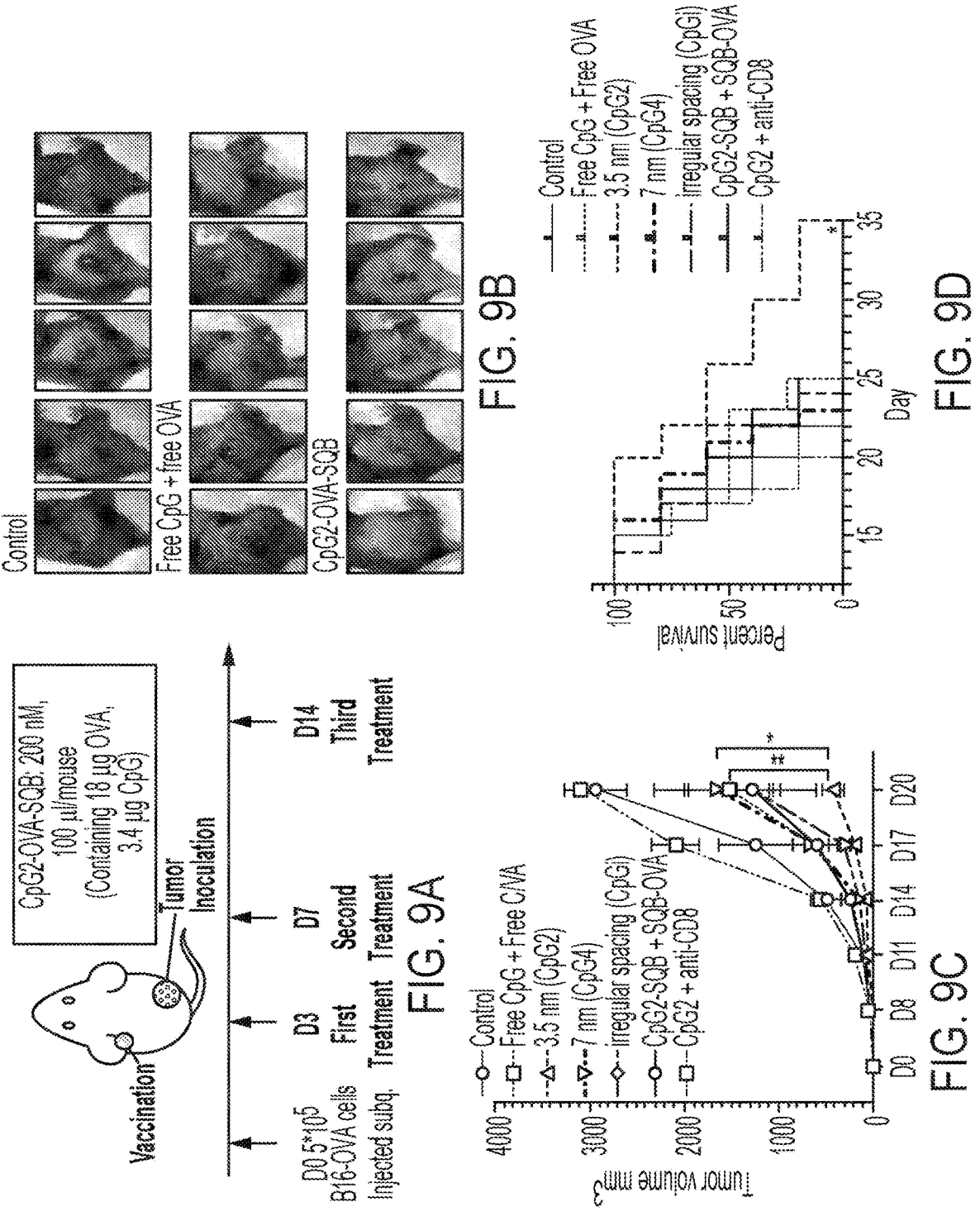

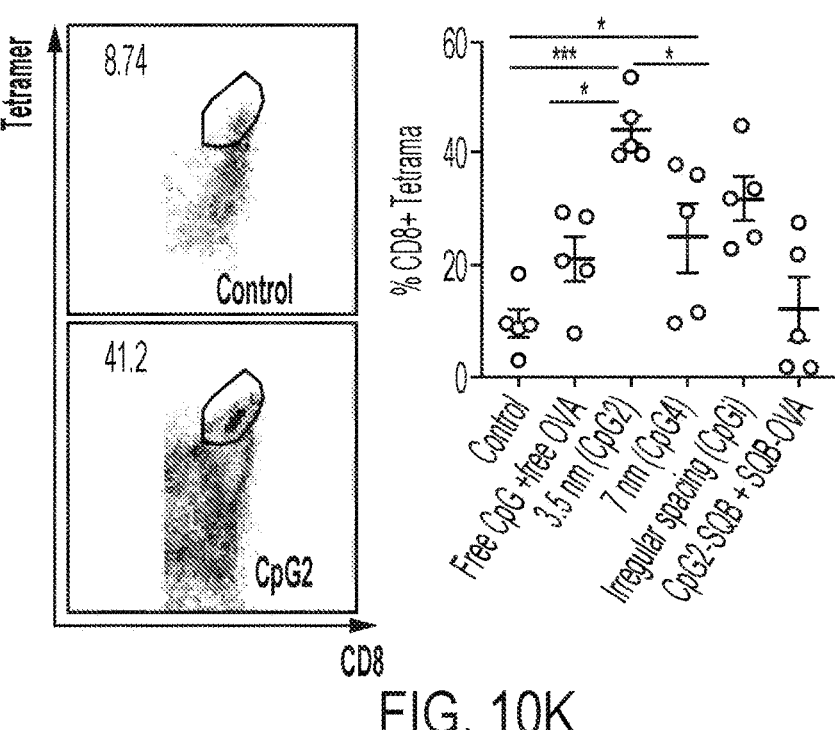
FIG. 10K
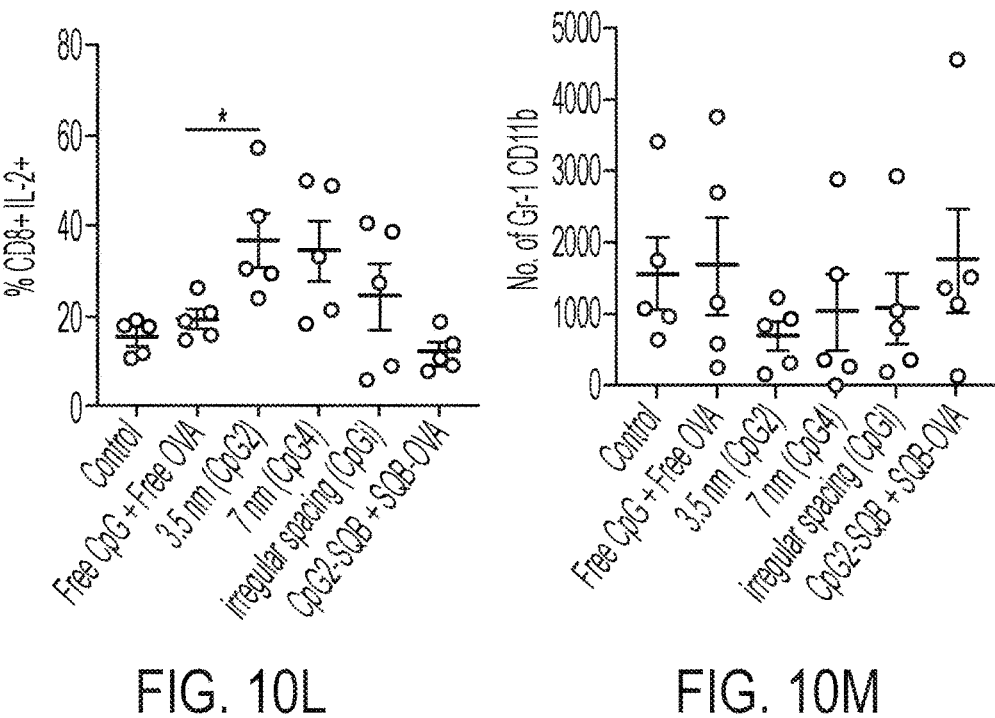
FIG. 10L                    FIG. 10M

DNA NANOSTRUCTURE-BASED VACCINES

RELATED APPLICATION

This application is a U.S. national stage application claiming the benefit of international application number PCT/US2020/036281, filed Jun. 5, 2020, which claims the benefit under 35 U.S.C. § 119 (e) of U.S. provisional application No. 62/858,783, filed Jun. 7, 2019, each of which is incorporated by reference herein in its entirety.

BACKGROUND

CpG oligodeoxynucleotides (CpG ODN) that bind toll-like receptor 9 (TLR9) on antigen-presenting cells such as dendritic cells (DCs) have been recognized as promising vaccine adjuvants for effective vaccination (Vaccine 32(48) (2014) 6377). As a result, many DC-based cancer vaccines in development have used CpG ODN in order to induce type 1 (Th1)-polarized immune responses which are associated with cytotoxic T lymphocytes-mediated killing of tumor cells. However, several studies indicated that CpG ODN induced a poorly focused T cell immune response containing both Th1 and Th2 immune responses. CpG spacing at the nanoscale has been known to play important roles in TLR9 activation and subsequent immune polarization to Th1 or Th2 responses (Cell Rep 18(3) (2017) 700).

SUMMARY

Provided herein in various aspects are DNA nanostructure-based vaccines (e.g., cancer vaccines) with an adjuvant (e.g., CpG) spatial distribution that elicits a Th1-polarized immune response. The data provided herein shows (1) that DNA origami—square-lattice blocks (SQBs) with different CpG spacing were successfully fabricated; (2) CpG-Cy5-SQBs prevent DCs from apoptosis and CpG at spacing of 3-5 nm (e.g., 3.5 nm) ('CpG2') showed optimal DC activation in terms of Th1 immune response polarization; and (3) ovalbumin (OVA) conjugated CpG-OVA-SQBs showed superior antigen uptake and CpG at spacing of 3-5 nm (e.g., 3.5 nm) induced an improved Th1 polarized immune response.

Some aspects herein provide CpG-SQBs personalized vaccines (e.g., using multiple antigenic peptides derived from several tumor models).

Some aspects of the present disclosure provide a nucleic acid nanostructure conjugated to an antigen, oligolysine-polyethylene glycol copolymer, and CpG ligand, wherein the CpG ligand is uniformly spaced on the nucleic acid nanostructure.

In some embodiments, the distance between any two adjacent molecules of CpG is 2 nm to 10 nm. For example, the distance between any two adjacent molecules of CpG may be 2-3 nm, 3-4 nm, 4-6 nm, or 6-8 nm. In some embodiments, the distance between any two adjacent molecules of CpG is a 2.5 nm, 3.5 nm, 5 nm, or 7 nm.

In some embodiments, the density of CpG ligand on the nucleic acid nanostructure is 1 molecule of CpG ligand per 5 to 50 nm$^2$.

In some embodiments, wherein the distance between any two adjacent molecules of CpG is 3.5 nm. Thus, in some embodiments, the density of CpG ligand on the nucleic acid nanostructure is 1 molecule of CpG ligand per 10 to 20 nm$^2$.

In some embodiments, the distance between any two adjacent molecules of CpG is 5 nm. Thus, in some embodiments, the density of CpG ligand on the nucleic acid nanostructure is 1 molecule of CpG ligand per 20 to 30 nm$^2$.

In some embodiments, the nucleic acid nanostructure comprises a two- or three-dimensional square-lattice structure.

In some embodiments, the CpG ligand is located on at least one surface of the nucleic acid nanostructure. In some embodiments, the antigen is located on at least one surface of the nucleic acid nanostructure. In some embodiments, the CpG ligand and the antigen are located on different surfaces of the nucleic acid nanostructure, relative to each other.

In some embodiments, the nucleic acid nanostructure comprises 5 to 25, 10 to 25, or 15 to 25 CpG ligand molecules. In some embodiments, the CpG ligands and/or antigen are located on a single surface of the nucleic acid nanostructure.

In some embodiments, the oligolysine-polyethylene glycol (PEG) copolymer comprises ten lysine residues and five PEG molecules (K10PEG5). In some embodiments, the oligolysine-PEG copolymer consists of ten lysine residues and five PEG molecules (K10PEG5).

In some embodiments, the antigen is covalently conjugated to the nanostructure. In some embodiments, the oligolysine-PEG copolymer is covalently conjugated to the nanostructure.

In some embodiments, the nucleic acid of the nanostructure comprises DNA, RNA, or a mixture of DNA and RNA. In some embodiments, the nucleic acid of the nanostructure comprises DNA. In some embodiments, the nucleic acid of the nanostructure consists of DNA.

Some aspects of the present disclosure provide a DNA nanostructure conjugated to an antigen, oligolysine-polyethylene glycol copolymer, and CpG ligand, wherein the DNA nanostructure comprises a three-dimensional square-lattice structure, the CpG ligand is uniformly spaced with a density of 1 molecule of CpG ligand per 10-30 nm$^2$, and the distance between any two adjacent molecules of CpG is 3-5 nm.

Other aspects of the present disclosure provide a method comprising delivering to a subject the nanostructure of any one of the preceding paragraphs in an effective amount to produce a CD8+ T cell immune response in the subject.

In some embodiments, the subject has a tumor. In some embodiments, the antigen is a tumor antigen.

In some embodiments, administration of the nanostructure results in an at least 2-fold or at least 3-fold reduction in tumor volume.

In some embodiments, administration of the nanostructure stimulates cytokine production in dendritic cells of the subject, wherein the cytokine production is at least 10%, at least 15%, or at least 20% higher than cytokine production by dendritic cells in a subject administered antigen only or antigen and free CpG ligand.

In some embodiments, administration of the nanostructure stimulates Interleukin-10 (IL10) and/or IL12 production in dendritic cells of the subject.

In some embodiments, administration of the nanostructure increases antigen uptake in dendritic cells of the subject, wherein the antigen uptake is at least 10%, at least 15%, or at least 20% higher than antigen uptake by dendritic cells in a subject administered antigen only or antigen and free CpG ligand.

In some embodiments, administration of the nanostructure stimulates a stronger Th1 immune response, relative to stimulation of a Th2 response.

In some embodiments, the Th1 immune response is characterized by expression of CD69 and CD8 on T cells.

In some embodiments, administration of the nanostructure stimulates CD8+ T cell proliferation by at least 10%, at least 15%, or at least 20% relative to CD8+ T cell proliferation in control cells in a subject administered antigen only or antigen and free CpG ligand.

In some embodiments, administration of the nanostructure stimulates IFN-γ expression in OT-I CD8+ T cells of the subject, wherein the IFN-γ expression is at least 10%, at least 15%, or at least 20% higher than IFN-γ expression by in OT-I CD8+ T cells in a subject administered antigen only or antigen and free CpG ligand.

In some embodiments, administration of the nanostructure increases DC maturation marker expression (e.g., by at least 10%, at least 20%, at least 30%, at least 40%, or at least 50%) relative to a control (e.g., antigen only or antigen and free CpG ligand).

In some embodiments, administration of the nanostructure increases the IL12/IL10 T cell production/secretion ratio (e.g., by at least 10%, at least 20%, at least 30%, at least 40%, or at least 50%) relative to a control (e.g., antigen only or antigen and free CpG ligand).

In some embodiments, administration of the nanostructure elevates MHC I peptide cross presentation (e.g., by at least 10%, at least 20%, at least 30%, at least 40%, or at least 50%) relative to a control (e.g., antigen only or antigen and free CpG ligand).

In some embodiments, administration of the nanostructure increases CD8 T cell proliferation (CFSE as an indicator for proliferation and IL-2 secretion) and activation (CD69 and IFNr secretion) (e.g., by at least 10%, at least 20%, at least 30%, at least 40%, or at least 50%) relative to a control (e.g., antigen only or antigen and free CpG ligand).

In some embodiments, administration of the nanostructure increases CD4 Th1 cell activation (IFNr) (e.g., by at least 10%, at least 20%, at least 30%, at least 40%, or at least 50%) relative to a control (e.g., antigen only or antigen and free CpG ligand).

In some embodiments, administration of the nanostructure does not results in an increase in production/proliferation of Treg CD4 cells.

In some embodiments, administration of the nanostructure increases CD69 positive T cells in vivo in the lymph node (e.g., by at least 10%, at least 20%, at least 30%, at least 40%, or at least 50%) relative to a control (e.g., antigen only or antigen and free CpG ligand).

In some embodiments, administration of the nanostructure increases CD44 memory T cells in vivo in the lymph node (e.g., by at least 10%, at least 20%, at least 30%, at least 40%, or at least 50%) relative to a control (e.g., antigen only or antigen and free CpG ligand)

In some embodiments, administration of the nanostructure increases tetramer CD8 T cells in vivo (corresponded to cross presentation and CD8 activation) in the lymph node (e.g., by at least 10%, at least 20%, at least 30%, at least 40%, or at least 50%) relative to a control (e.g., antigen only or antigen and free CpG ligand).

In some embodiments, administration of the nanostructure increases infiltrated T cells (e.g., by at least 10%, at least 20%, at least 30%, at least 40%, or at least 50%) relative to a control (e.g., antigen only or antigen and free CpG ligand).

In some embodiments, administration of the nanostructure increases tetramer CD8 T cells in vivo in the tumor (e.g., by at least 10%, at least 20%, at least 30%, at least 40%, or at least 50%) relative to a control (e.g., antigen only or antigen and free CpG ligand).

BRIEF DESCRIPTION OF THE DRAWINGS

FIGS. 3A-3F include data relating to cellular uptake of PEG-purified and K10PEG5-coated CpG-Cy5-SQBs. See Example 2.

FIGS. 4A-4H include data relating to dendritic cell maturation and Th1 immune response polarization. See Example 3.

FIGS. 5A-5F include data relating to antigen uptake and presentation. See Example 4.

FIGS. 9A-9G show data relating to therapeutic and prophylactic effects in a mouse melanoma tumor model. See Example 8.

FIGS. 10A-10M show data relating to immune cell profiling in animals post vaccination. See Example 9.

DETAILED DESCRIPTION

Figure 1:
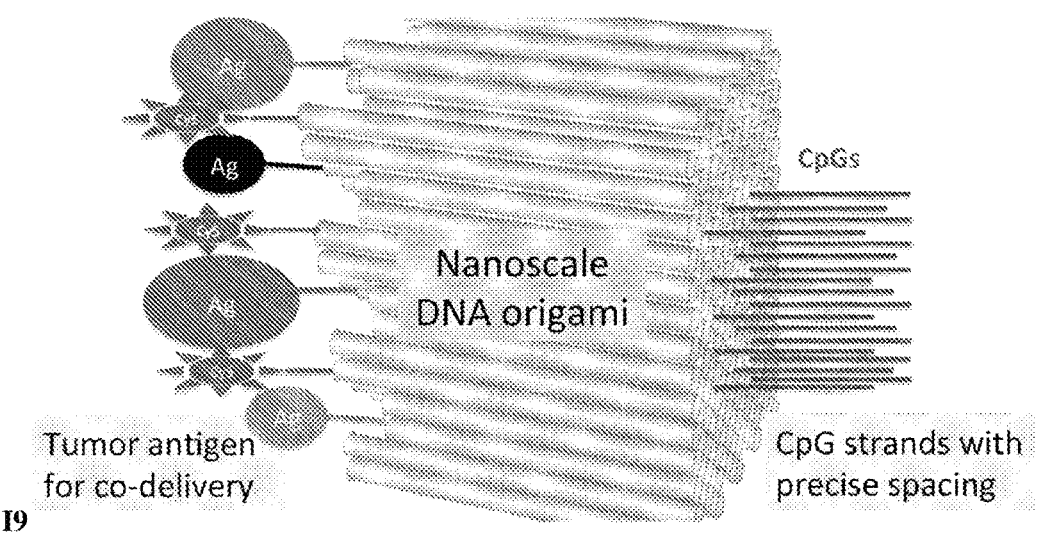
FIG. 1 is a schematic depicting a DNA origami nanostructure as a unique platform for co-delivery of multiple antigens and adjuvant (e.g., CpG) with precise nanoscale distribution.

In some aspects, the present disclosure provides a nucleic acid (e.g., DNA) nanostructure comprising a plurality (e.g., 10, 20, 50, 100, 1000, 10,000, 10-20, 10-50, 10-100, 10-1000, 10-1000, 100-1000, 100-10000, or 1000-10000) of uniformly spaced CpG ligands and a plurality (e.g., 10, 20, 50, 100, 1000, 10,000, 10-100, 10-1000, 10-1000, 100-1000, 100-10000, or 1000-10000) of antigens, wherein the nucleic acid nanostructure is coated and covalently crosslinked with oligolysine-polyethylene glycol (PEG) copolymer.

In some embodiments, a nucleic acid nanostructure comprises at least 5, at least 10, or at least 20 adjuvant (e.g., CpG ligand) molecules. In some embodiments, a nucleic acid nanostructure comprises at least 5 but less than 65 adjuvant (e.g., CpG ligand) molecules. For example, a nucleic acid nanostructure may comprise 5-55, 5-50, 5-45, 5-40, 5-35, 5-30, 5-35, 5-20, 10-55, 10-50, 10-45, 10-40, 10-35, 10-30, 10-35, 10-20, 15-55, 15-50, 15-45, 15-40, 15-35, 15-30, 15-35, or 15-20 adjuvant (e.g., CpG ligand) molecules. In some embodiments, the nucleic acid nanostructure comprises 5 to 25, 10 to 25, or 15 to 25 adjuvant (e.g., CpG ligand) molecules. In some embodiments, a nucleic acid nanostructure comprises 5, 6, 7, 8, 9, 10, 11, 12, 13, 14, 15, 16, 17, 18, 19, or 20 adjuvant (e.g., CpG ligand) molecules. In some embodiments, a nucleic acid nanostructure comprises 18 adjuvant (e.g., CpG ligand) molecules.

In some embodiments, each CpG ligand of the plurality of CpG ligands is uniformly spaced 2.0 nm, 2.5 nm, 3.0 nm, 3.5 nm, 4.0 nm, 4.5 nm, 5 nm, 5.5 nm, 6 nm, 6.5 nm, or 7 nm from any other adjacent CpG ligand. In some embodiments, each CpG ligand of the plurality of CpG ligands is uniformly spaced 3.5 nm from any other adjacent CpG ligand. In some embodiments, each CpG ligand of the plurality of CpG ligands is uniformly spaced 5 nm from any other adjacent CpG ligand. In some embodiments, each CpG ligand of the plurality of CpG ligands is uniformly spaced 2 nm-10 nm, 2.5 nm-10 nm, 3 nm-10 nm, 3.5 nm-10 nm, 4 nm-10 nm, 4.5 nm-10 nm, 5 nm-10 nm, 5.5 nm-10 nm, 6 nm-10 nm, 6.5 nm-10 nm, 7 nm-10 nm, 7.5 nm-10 nm, 8 nm-10 nm, 8.5 nm-10 nm, 9 nm-10 nm, 9.5 nm-10 nm from any other adjacent CpG ligand.

In some aspects, the present disclosure provides a nucleic acid nanostructure comprising a plurality of CpG ligands and a plurality of antigens, wherein each CpG ligand of the plurality of CpG ligands is uniformly spaced 3.5 nm from any other CpG ligand.

Figure 2:
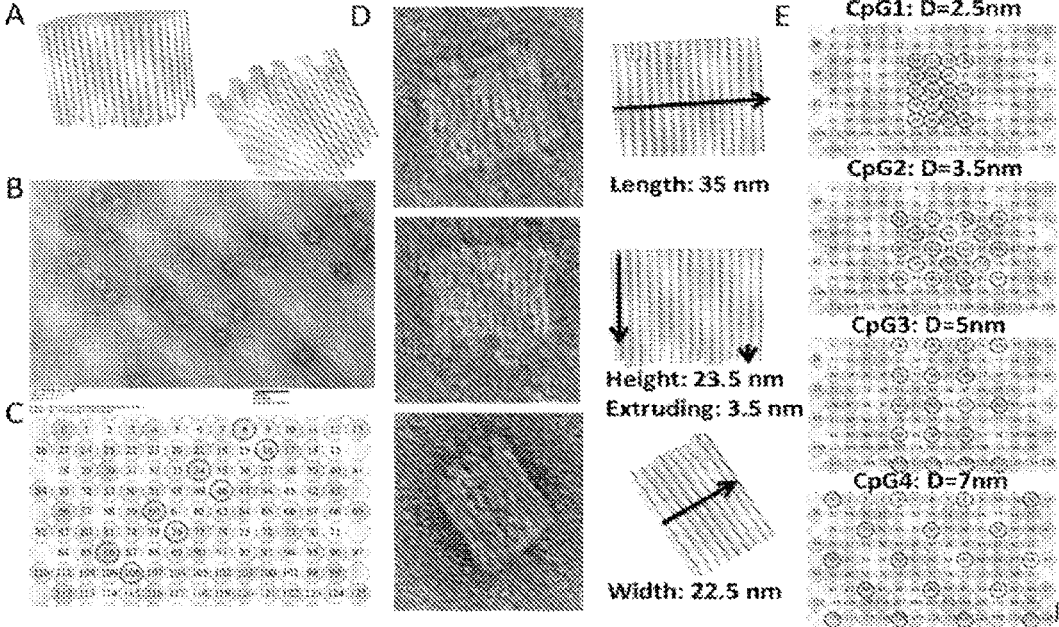
FIGS. 2A-2E include data relating to Cadnano design and folding of square-lattice-blocks (SQBs). See Example 1.

In some embodiments, the distance between any two adjacent molecules of adjuvant (e.g., CpG ligand) is 2 nm-10 nm. For example, the distance between any two adjacent molecules of adjuvant (e.g., CpG ligand) may be 2-3 nm, 3-4 nm, 4-6 nm, or 6-8 nm. In some embodiments, the distance between any two adjacent molecules of adjuvant (e.g., CpG ligand) is a 2.5 nm, 3.5 nm, 5 nm, or 7 nm. Uniform spacing herein refers to the distance between any two adjacent molecules, measuring from the center of the molecule. With reference to FIG. 2E, for example, the outlined circles represent individual CpG ligands, and the distance between the center of two adjacent CpG ligands is 2.5 nm, 3.5 nm, 5 nm, and 7 nm, top to bottom images, respectively.

In some embodiments, the density of adjuvant (e.g., CpG ligand) on the nucleic acid nanostructure is 1 molecule of adjuvant (e.g., CpG ligand) per 5 to 50 nm$^2$.

In some embodiments, the distance between any two adjacent molecules of adjuvant (e.g., CpG ligand) is 2.5 nm. In some embodiments, the density of adjuvant (e.g., CpG ligand) on the nucleic acid nanostructure is 1 molecule of adjuvant (e.g., CpG ligand) per 5 to 10 nm$^2$. In some embodiments, the density of adjuvant (e.g., CpG ligand) on the nucleic acid nanostructure is 1 molecule of adjuvant (e.g., CpG ligand) per 5, 5.5, 6, 6.5, 7, 7.5, 8, 8.5, 9, 9.5, or 10 nm$^2$.

In some embodiments, the distance between any two adjacent molecules of adjuvant (e.g., CpG ligand) is 3.5 nm. In some embodiments, the density of adjuvant (e.g., CpG ligand) on the nucleic acid nanostructure is 1 molecule of adjuvant (e.g., CpG ligand) per 10 to 20 nm$^2$. For example, the density of adjuvant (e.g., CpG ligand) on the nucleic acid nanostructure may be 10 to 15 nm$^2$. In some embodiments, the density of adjuvant (e.g., CpG ligand) on the nucleic acid nanostructure is 1 molecule of adjuvant (e.g., CpG ligand) per 10, 10.5, 11, 11.5, 12, 12.5, 13, 13.5, 14, 14.5, or 15 nm$^2$.

In some embodiments, the distance between any two adjacent molecules of adjuvant (e.g., CpG ligand) is 5 nm. In some embodiments, the density of adjuvant (e.g., CpG ligand) on the nucleic acid nanostructure is 1 molecule of adjuvant (e.g., CpG ligand) per 20 to 30 nm$^2$. In some embodiments, the density of adjuvant (e.g., CpG ligand) on the nucleic acid nanostructure is 1 molecule of adjuvant (e.g., CpG ligand) per 20, 20.5, 21, 21.5, 22, 22.5, 23, 23.5, 24, 24.5, 25, 25.5, 26, 26.5, 27, 27.5, 28, 28.5, 29, 29.5, or 30 nm$^2$.

In some embodiments, the distance between any two adjacent molecules of adjuvant (e.g., CpG ligand) is 7 nm. In some embodiments, the density of adjuvant (e.g., CpG ligand) on the nucleic acid nanostructure is 1 molecule of adjuvant (e.g., CpG ligand) per 45 to 55 nm$^2$. In some embodiments, the density of adjuvant (e.g., CpG ligand) on the nucleic acid nanostructure is 1 molecule of adjuvant (e.g., CpG ligand) per 45, 45.5, 46, 46.5, 47, 47.5, 48, 48.5, 49, 9.5, 50, 50.5, 51, 51.5, 52, 52.5, 53, 53.5, 54, 54.5, or 55 nm$^2$.

In some embodiments, the nucleic acid nanostructure is coated and covalently crosslinked with oligolysine-polyethylene glycol (PEG) copolymer.

In some embodiments, the nucleic acid nanostructure is a nucleic acid (e.g., DNA) origami nanostructure. In some embodiments, the nucleic acid (e.g., DNA) origami nanostructure is a 126-helix nucleic acid (e.g., DNA) origami nanostructure. In some embodiments, the nucleic acid nanostructure is a nucleic acid (e.g., DNA) single-stranded tile (SST) nanostructure.

In some embodiments, the plurality of antigens comprise ovalbumin.

In some embodiments, the plurality of antigens are covalently linked to the nanostructure. In some embodiments, the plurality of antigens are covalently linked to free amine groups of the nucleic acid nanostructure.

In some aspects, the present disclosure provides a method of inducing a Th1 polarized immune response in cells, the method comprising administering to a subject (e.g., a human subject) the nucleic acid nanostructure provided herein.

In some aspects, the present disclosure provides a method of inducing a Th1 polarized immune response in cells, the method comprising administering to a subject a nucleic acid nanostructure comprising a plurality of uniformly spaced CpG ligands and a plurality of antigens.

In some embodiments, the volume of the tumor is reduced at least 2-fold, at least 3-fold, at least 4-fold, at least 5-fold, relative to control (e.g., wherein the control is free CpG+free antigen+free nanostructure, or wherein the control is buffer only). In some embodiments, the volume of the tumor is reduced 2-fold, 3-fold, 4-fold, or 5-fold relative to control.

In some embodiments, the nucleic acid nanostructure is administered to the subject multiple times (e.g., at least 2 times, at least 3 times, etc.).

Oligolysine-Polyethylene Glycol (PEG) Copolymer

Aspects of the present disclosure provide nucleic acid nanostructures covalently coated with oligolysine-PEG copolymer (oligolysine comprising lysine amino acids and PEG moieties) that protect the nanostructures from degradation, for example, under physiological conditions of magnesium and/or calcium depletion and nuclease activity. Nucleic acid nanostructures, in general, typically require up to 16 mM magnesium ion (Mg$^{2+}$) to neutralize electrostatic repulsion and thereby stabilize their shape. Thus, such structures exhibit poor structural integrity in biological buffers (e.g., buffers containing physiological levels of Mg$^{2+}$ (e.g., 0.6 mM) and Ca$^{2+}$ (e.g., 1.2 mM)). Further, the activity of DNAse I in freshly prepared cell medium containing 10% fetal bovine serum, which is typically used in biomedical applications, causes rapid degradation of nucleic acid nanostructures. The structural integrity of nucleic acid nanostructures can be maintained, even under physiological conditions (e.g., including low salt conditions), by linking the nanostructures to positively charged oligolysine (e.g., oligolysine-PEG copolymer), which neutralize electrostatic repulsion and enhance nucleic acid resistance to nuclease degradation, thereby stabilizing the shape of the nanostructures.

Nucleic acid nanostructures may be covalently coated with oligolysine-PEG copolymer such that the covalent crosslink occurs between an oligolysine-PEG copolymer and the nucleic acid nanostructure involves the amine of a lysine amino acid side chain of the polylysine polymer. The covalent crosslink may be formed using an aldehyde crosslinking agent or any suitable crosslinking agent. In some embodiments, an aldehyde crosslinking agent is formaldehyde or glutaraldehyde.

Nucleic acid nanostructures may be covalently coated with oligolysine such that the covalent crosslink occurs between any atom of an oligolysine and any atom of the nucleic acid nanostructure. In some embodiments, the covalent crosslink is formed using a nucleic acid crosslinking agent. In some embodiments, a nucleic acid crosslinking agent is cisplatin or methoxypsoralen (8-MOP).

Oligolysine-PEG copolymer of the present invention is a cationic polymer, which, without being bound by any particular theory, may be used to shield the negatively charged phosphate backbone of nucleic acids, thereby promoting close packing of nucleic acid helices to stabilize the shape of and slow down nuclease degradation of the nanostructures.

Oligolysine-PEG copolymer may comprise any one or more functional groups in addition to its primary amine groups. As used herein, a "functional group" refers to an atom or group of atoms, such as a carboxyl group, that replaces hydrogen in an organic compound and determines the chemical behavior of the compound. Examples of common functional groups include, without limitation, alkane, ether, ketone, alkene, aldehyde, alkyne, imine, carboxylic acid, alkyl halide, ester, alcohol, thioester, thiol, amide, acyl phosphate, acid chloride, thioether, phosphate monoester, phenol and phosphate diester. Oligolysine of the present disclosure include linear, branched and dendrimer polymers. Oligolysine of the present disclosure, in some embodiments, are not limited by length of the polymer.

The length of oligolysine-PEG copolymer may vary. In some embodiments, the length of an oligolysine is 5-100 lysines (i.e., the oligolysine comprise 5-100 lysines). For example, the length of an oligolysine may be 5-75, 5-50, 5-25, 5-20, 5-25, or 5-10 lysines. In some embodiments, the length of an oligolysine is 5, 10, 15, 20, 25, 30, 35, 40, 45, 50, 55, 60, 65, 70, 75, 80, 85, 90, 95, or 100 lysines.

In some embodiments, an oligolysine-PEG copolymer includes one or more additional amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine) and/or analogs thereof. Thus, oligolysine may comprise or consist of peptides (e.g., short chains of amino acid monomers linked by peptide (e.g., amide) bonds). In some embodiments, oligolysine-PEG copolymer comprise positively charged amino acids such as lysine and/or arginine. In some embodiments, the oligolysine-PEG copolymer may comprise poly-L-lysine polymers.

In some embodiments, an oligolysine-PEG copolymer comprises a plurality of lysines. In some embodiments, an oligolysine-PEG copolymer comprises at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% lysine amino acids. In some embodiments, a region of amino acids comprises 50% to 100%, 55% to 100%, 60% to 100%, 65% to 100%, 70% to 100%, 75% to 100%, 80% to 100%, 85% to 100% or 90% to 100% lysine amino acids.

Lysines of oligolysine-PEG copolymer, in some embodiments, are separated from each other by at least 1, at least 2, at least 3, at least 4, at least 5, at least 6, at least 7, at least 8, at least 9, at least 10 or more, non-amine containing amino acids such as non-lysine amino acids. In some embodiments, lysines of oligolysine-PEG copolymer are separated from each other by 1 to 5, or 1 to 10, non-amine containing amino acids such as non-lysine amino acids. In some embodiments, lysines of oligolysine-PEG copolymer are regularly spaced. The following are non-limiting examples of linear oligolysine having regularly-spaced lysine (K), where X is a non-lysine amino acid, or functional group, and n is any integer equal to or greater than 1:

(i) K-X-(K-X-)$_n$-K, or X-(K-X-)$_n$, K-X-(K-X-)$_n$, or X-(K-X-)$_n$-K;

(ii) K-X-X-(K-X-X-)$_n$-K, or X-X-(K-X-X-)$_n$, or K-X-X-(K-X-X-)$_n$, or X-X-(K-X-X-)$_n$-K; or (iii) K-X-X-X-(K-X-X-X-)$_n$-K, or X-X-X-(K-X-X-X)$_n$, or K-X-X-X-(K-X-X-X-)$_n$, or X-X-X-(K-X-X-X-)$_n$K.

In some embodiments, the oligolysine herein comprise a polyethylene glycol (PEG) moiety or a related ether-containing functional group. A PEG moiety may comprise at least 5, at least 10, at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1250, at least 1500, or at least 2000 polyethylene glycol monomer units. In some embodiments, a PEG moiety may comprise 5-100, 50-100, 50-200, 100-200, 100-150, 200-250, 200-300, 250-500, 400-600, 500-1000, 750-1000, 750-1500, or 1250-2000 polyethylene glycol monomer units. In some embodiments, a PEG moiety is PEG 1K (average molecular weight of 1000 Daltons), PEG 5K (average molecular weight of 5000 Daltons), PEG 10K (average molecular weight of 10000 Daltons), PEG 20K (average molecular weight of 20000 Daltons), PEG 25K (average molecular weight of 25000 Daltons), PEG 50K (average molecular weight of 50000 Daltons), or PEG 100K (average molecular weight of 100000 Daltons).

Nucleic Acid Nanostructures

A "nucleic acid nanostructure," as used herein, refers to nucleic acids that form (e.g., self-assemble) two-dimensional (2D) or three-dimensional (3D) shapes (e.g., reviewed in W. M. Shih, C. Lin, *Curr. Opin. Struct. Biol.* 20, 276 (2010), incorporated by reference herein). Nanostructures may be formed using any nucleic acid folding or hybridization methodology. One such methodology is DNA origami (see, e.g., Rothmund, P. W. K. *Nature* 440 (7082): 297-302 (2006), incorporated by reference herein). In a DNA origami approach, a nanostructure is produced by the folding of a longer "scaffold" nucleic acid strand through its hybridization to a plurality of shorter "staple" oligonucleotides, each of which hybridize to two or more non-contiguous regions within the scaffold strand. In some embodiments, a scaffold strand is at least 100 nucleotides in length. In some embodiments, a scaffold strand is at least 500, at least 1000, at least 2000, at least 3000, at least 4000, at least 5000, at least 6000, at least 7000, or at least 8000 nucleotides in length. The scaffold strand may be naturally or non-naturally occurring. Staple strands are typically less than 100 nucleotides in length; however, they may be longer or shorter depending on the application and depending upon the length of the scaffold strand. In some embodiments, a staple strand may be 15 to 100 nucleotides in length. In some embodiments, a staple strand is 25 to 50 nucleotides in length.

In some embodiments, a nucleic acid nanostructure may be assembled in the absence of a scaffold strand (e.g., a scaffold-free structure). For example, a number of oligonucleotides (e.g., less than 200 nucleotides or less than 100 nucleotides in length) may be assembled to form a nucleic acid nanostructure.

Other methods for assembling nucleic acid nanostructures are known in the art, any one of which may be used herein. Such methods are described by, for example, Bellot G. et al., *Nature Methods,* 8: 192-194 (2011); Liedl T. et al, *Nature Nanotechnology,* 5: 520-524 (2010); Shih W. M. et al, *Curr.*

*Opin. Struct. Biol.,* 20: 276-282 (2010); Ke Y. et al, *J. Am. Chem. Soc,* 131: 15903-08 (2009); Dietz H. et al, *Science,* 325: 725-30 (2009); Hogberg B. et al, *J. Am. Chem. Soc,* 131: 9154-55 (2009); Douglas S. M. et al, *Nature,* 459: 414-418 (2009); Jungmann R. et al, *J. Am. Chem. Soc,* 130: 10062-63 (2008); Shih W. M., *Nature Materials,* 7: 98-100 (2008); and Shih W. M., *Nature,* A11: 618-21 (2004), each of which is incorporated herein by reference in its entirety.

A nucleic acid nanostructure may be assembled into one of many defined and predetermined shapes including without limitation a capsule, hemi-sphere, a cube, a cuboidal, a tetrahedron, a cylinder, a cone, an octahedron, a prism, a sphere, a pyramid, a dodecahedron, a tube, an irregular shape, and an abstract shape. The nanostructure may have a void volume (e.g., it may be partially or wholly hollow). In some embodiments, the void volume may be at least 25%, at least 50%, at least 75%, at least 85%, at least 90%, or more of the volume of the nanostructure. Thus, in some embodiments, nucleic acid nanostructures do not comprise a solid core. In some embodiments, nucleic acid nanostructures are not circular or near circular in shape. In some embodiments, nucleic acid nanostructures are not a solid core sphere. Depending on the intended use, nucleic acid nanostructures may be assembled into a shape as simple as a two-dimensional sheet or as complex as a three-dimensional capsule or lattice (or even more complex).

In some embodiments, the nucleic acid nanostructure comprises a two- or three-dimensional square-lattice structure. A description of three-dimensional square-lattice structure is described in Yonggang Ke et al., Multilayer DNA Origami Packed on a Square Lattice. J Am Chem Soc. 2009 Nov. 4; 131(43):15903-8, incorporated herein in its entirety.

Nucleic acid nanostructures may be made of, or comprise, DNA, RNA, modified DNA, modified RNA, PNA, LNA or a combination thereof.

In some embodiments, nucleic acid nanostructures are rationally designed. A nucleic acid nanostructure is herein considered to be "rationally designed" if nucleic acids that form the nanostructure are selected based on pre-determined, predictable nucleotide base pairing interactions that direct nucleic acid hybridization. For example, nucleic acid nanostructures may be designed prior to their synthesis, and their size, shape, complexity and modification may be prescribed and controlled using certain select nucleotides (e.g., oligonucleotides) in the synthesis process. The location of each nucleic acid in the structure may be known and provided for before synthesizing a nanostructure of a particular shape. The fundamental principle for designing, for example, self-assembled nucleic acid nanostructures is that sequence complementarity in nucleic acid strands is selected such that, by pairing up complementary segments, the nucleic acid strands self-organize into a predefined nanostructure under appropriate physical conditions. Thus, in some embodiments, nucleic acid nanostructures are self-assembling. Similarly, handles and anti-handle nucleic acids (e.g., those linked to adjuvant and/or antigen) may be rationally designed to attach specifically to an interior or exterior surface of a nanostructure, in some embodiments, without intercalation or hybridization with nucleic acids forming the body of the nanostructure.

Examples of nucleic acid nanostructures for use in accordance with the present disclosure include, without limitation, capsules, lattices (E. Winfree, et al. *Nature* 394, 539 (1998); H. Yan, et al. *Science* 301, 1882 (2003); H. Yan, et al. *Proc. Natl. Acad. of Sci. USA* 100, 8103 (2003); D. Liu, et al. *J. Am. Chem. Soc.* 126, 2324 (2004); P. W. K. Rothemund, et al. *PLoS Biology* 2, 2041 (2004)), ribbons (S.

H. Park, et al. *Nano Lett.* 5, 729 (2005); P. Yin, et al. *Science* 321, 824 (2008)), tubes (H. Yan *Science* (2003); P. Yin (2008)), finite two-dimensional (2D) and three dimensional (3D) objects with defined shapes (J. Chen, N. C. Seeman, *Nature* 350, 631 (1991); P. W. K. Rothemund, *Nature* 440, 297 (2006); Y. He, et al. *Nature* 452, 198 (2008); Y. Ke, et al. *Nano. Lett.* 9, 2445 (2009); S. M. Douglas, et al. *Nature* 459, 414 (2009); H. Dietz, et al. *Science* 325, 725 (2009); E. S. Andersen, et al. *Nature* 459, 73 (2009); T. Liedl, et al. *Nature Nanotech.* 5, 520 (2010); D. Han, et al. *Science* 332, 342 (2011)), and macroscopic crystals (J. P. Meng, et al. *Nature* 461, 74 (2009)). Other nucleic acid nanostructures may be used as provided herein.

Cadnano software may be used to design particular nucleic acid nanostructures of interest (see cadnano.org).

Polylysine, a cationic polymer, is known to be efficient in condensing plasmid DNA into compact particles, for example, for delivery of therapeutic DNA. DNA is a highly negatively charged polymer due to the repeating phosphate groups along the polymer backbone. The interaction with cationic polymers such as polylysine is therefore an electrostatic one. It is generally accepted that DNA condensation occurs through neutralization of negative charges on the DNA by its interactions with cationic oligolysine, followed by hydrophobic collapse as water is displaced from the DNA structure. Generally, DNA is super-saturated with oligolysine such that most or all of the negative charges of the DNA are neutralized, and the DNA condenses into a compact particle of 12 nm to 300 nm in diameter, depending on the weight of the polylysine polymer and the condensation conditions (e.g., charge ratio between polymer and DNA, salt concentration and temperature). In some embodiments, the term "condensed nucleic acid" refers to a nucleic acid particle that has a diameter and/or volume that is less than 80%, less than 70%, less than 60%, less than 50%, or less than 40% of the diameter and/or volume of its non-condensed state (e.g., without being supersaturated with polylysine). Unlike the condensed, compacted DNA particles described above, the nucleic acid nanostructures of the present disclosure are not condensed into compact particles when complexed with oligolysine in accordance with the present disclosure. Rather, nucleic acid nanostructures provided herein maintain their structure integrity. In some embodiments, the nucleic acid nanostructures are "subsaturated" or "saturated" with covalently linked oligolysine (e.g., coated with oligolysine at a N:P (nitrogen in lysine to phosphorus in nucleic acid) ratio of 0.1:1 to 1:1) such that the architecture of the structures is not compromised. That is, nucleic acid nanostructures of the present disclosure have a 2D or 3D shape, despite the additional weight of and covalent interactions with positively-charged oligolysine.

Thus, nucleic acid nanostructures provided herein, in some embodiments, are subsaturated with oligolysine-PEG copolymer (e.g., coated with oligolysine-PEG copolymer at a N:P (nitrogen in lysine to phosphorus in nucleic acid) ratio of 0.1:1 to 0.95:1). As discussed above, nucleic acid nanostructures are considered to be "subsaturated" with oligolysine-PEG copolymer if less than 100% of the phosphates of the nucleic acid nanostructure backbone are linked to amines of oligolysine-PEG copolymer. In some embodiments, less than 98%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15% or less than 10% of the phosphates of nucleic acid nanostructure are linked to amines of the oligolysine-PEG copolymer. In some embodiments, 10% to 90%, 10% to 80%, 10% to 50%, 20% to 90%, or 20% to 80% of the phosphates of the nucleic acid nanostructure backbone are linked to amines of oligolysine-PEG copolymer. Further, as discussed above, nucleic acid nanostructures are considered to be "subsaturated" with oligolysine-PEG copolymer if, nanostructures are coated with oligolysine-PEG copolymer at a N:P ratio of 0.1:1, 0.2:1, 0.3:1, 0.4:1, 0.5:1, 0.6:1, 0.7:1, 0.8:1, 0.9:1, or 0.95:1. In some embodiments, nucleic acid nanostructures provided herein are saturated with oligolysine-PEG copolymer (e.g., coated with oligolysine at a N:P (nitrogen in lysine to phosphorus in nucleic acid) ratio of 1:1). Thus, in some embodiments, nanostructures are coated with oligolysine-PEG copolymer at a N:P ratio of 0.1:1 to 1:1, 0.2 to 1:1, 0.3 to 1:1, 0.5 to 1:1, 0.75:1:1, 0.9:1 to 1:1, 0.95:1 to 1:10.1:1 to 0.95:1, 0.2:1 to 0.95:1, 0.5:1 to 0.95:1, 0.1:1 to 0.3:1, 0.2:1 to 0.4:1, 0.4:1 to 0.5:1, 0.5:1 to 0.75:1, 0.5:1 to 0.8:1, 0.6:1 to 0.8:1, 0.7:1 to 0.95:1, 0.8:1 to 0.95:1, or 0.9:1 to 0.95:1. At such subsaturated or saturated levels, nucleic acid nanostructures still maintain their structural integrity (e.g., keep their original shape), despite their interactions with oligolysine-PEG copolymer. It should be understood that a nucleic acid nanostructure coated in oligolysine-PEG copolymer is herein considered to "maintain its structural integrity" if the shape of the nanostructure, under the same environmental conditions, can be distinguished/discerned for a period of time that is greater than that of a control nucleic acid nanostructure (e.g., a similar nucleic acid nanostructure that is not coated with oligolysine-PEG copolymer).

Surprisingly, nucleic acid nanostructures that are covalently linked to oligolysine-PEG copolymer as described herein are even more structurally stable and are more resistant to degradation (e.g., at low and/or physiological salt concentrations, in presence of nucleases) than nanostructures that are non-covalently linked to oligolysine-PEG copolymer. In some embodiments, nucleic acid nanostructures that are covalently linked to oligolysine-PEG copolymer are at least 2-fold, at least 5-fold, at least 10-fold, at least 20-fold, at least 50-fold, at least 100-fold, at least 150-fold, at least 180-fold, or at least 200-fold more resistant to degradation (e.g., nuclease degradation, e.g., in the presence of DNAseI nuclease) than nanostructures that are non-covalently linked to oligolysine-PEG copolymer.

The relationship between amines of oligolysine-PEG copolymer and phosphates of nucleic acid nanostructures may be described in terms of an amine to phosphate ratio. The "N/P ratio," herein, refers is the ratio of positive (+) charges contributed to a structure by a primary, secondary or tertiary amine that can be protonated (e.g., in the side chain of a lysine) to negative (−) charges contributed to a nanostructure by phosphates of its nucleic acid backbone. For example, lysine in the middle of a peptide contributes 1+ charge, while lysine at the N-terminus of a peptide contributes 2+ charges. Thus, "subsaturated," refers to a N:P ratio of 0.95:1 or lower (i.e., lower number of amines compared to phosphates). "Saturated," by comparison, refers to a N:P ratio of 1:1 (i.e., the same number of amine compared to phosphates). "Supersaturated" refers to a N:P ratio of 1.05:1 or greater (i.e., greater number of amines compared to phosphates). Thus, in some embodiments, the ratio of amines or amines to phosphate (e.g., amines of oligolysine-PEG copolymer that interact with (e.g., are linked to) phosphates of a nucleic acid nanostructure backbone) is lower than 1:1. For example, the ratio of amines phosphates may be 0.9:1, 0.8:1, 0.7:1, 0.6:1, 0.5:1, 0.4:1, 0.3:1, 0.2:1 or 0.1:1. In some embodiments, the ratio of amines to phosphates is 0.9:1 to 0.1:1, 0.9:1 to 5:1, 0.8:1 to 0.1:1 or 0.5:1 to 0.1:1. In some embodiments, the ratio of amines to phosphates is 1:1.

In some embodiments, the ratio of amines or amines to phosphate (e.g., amines of oligolysine-PEG copolymer that interact with (e.g., are linked to) phosphates of a nucleic acid nanostructure backbone) is 1:1.

As used herein, the terms "nucleic acid" and/or "oligonucleotide" may refer to at least two nucleotides covalently linked together. A nucleic acid of the present disclosure may generally contain phosphodiester bonds, although in some cases, nucleic acid analogs are included that may have other backbones, comprising, for example, phosphoramide (Beaucage et al., *Tetrahedron* 49(10):1925 (1993) and references therein; Letsinger, J. *Org. Chem.* 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphophoroamidite linkages (see Eckstein, *Oligonucleotides and Analogues: A Practical Approach*, Oxford University Press), and peptide nucleic acid backbones and linkages (see Egholm, *J. Am. Chem. Soc.* 114:1895 (1992); Meier et al., *Chem. Int. Ed. Engl.* 31:1008 (1992); Nielsen, *Nature,* 365:566 (1993); Carlsson et al., *Nature* 380:207 (1996), all of which are incorporated by reference). Other analog nucleic acids include those with positive backbones (Denpcy et al., *Proc. Natl. Acad. Sci. USA* 92:6097 (1995); non-ionic backbones (U.S. Pat. Nos. 5,386,023, 5,637,684, 5,602,240, 5,216,141 and 4,469,863; Kiedrowshi et al., Angew. *Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "Carbohydrate Modifications in Antisense Research", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., *Chem. Soc. Rev.* (1995) pp 169-176). Several nucleic acid analogs are described in Rawls, C & E News Jun. 2, 1997 page 35. All of these references are hereby expressly incorporated by reference. Nucleic acid may have a homogenous backbone (e.g., entirely phosphodiester or entirely phosphorothioate) or a heterogeneous (or chimeric) backbone. Phosphorothioate backbone modifications render a nucleic acid less susceptible to nucleases and thus more stable (as compared to a native phosphodiester backbone nucleic acid) under certain conditions. Other linkages that may provide more stability to a nucleic acid include without limitation phosphorodithioate linkages, methylphosphonate linkages, methylphosphorothioate linkages, boranophosphonate linkages, peptide linkages, alkyl linkages, dephospho type linkages, and the like. Thus, in some instances, nucleic acids have non-naturally occurring backbones. Modifications of the ribose-phosphate backbone may be done, for example, to facilitate the addition of labels, or to increase the stability and half-life of such molecules in physiological environments.

Nucleic acids may be single-stranded (ss) or double-stranded (ds), as specified, or may contain portions of both single-stranded and double-stranded sequence (e.g., are partially double-stranded). Nucleic acids may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, and isoguanine. As used herein, the term "nucleoside" includes nucleotides as well as nucleoside and nucleotide analogs, and modified nucleosides such as amino modified nucleosides. In addition, "nucleoside" includes non-naturally occurring analog structures. Thus, for example, the individual units of a peptide nucleic acid, each containing a base, are referred to herein as a nucleoside.

Nucleic acids include DNA such as B-form DNA, D-form DNA and L-form DNA and RNA, as well as various modifications thereof. Modifications include base modifications, sugar modifications, and backbone modifications. Non-limiting examples of these are provided below.

Non-limiting examples of DNA variants that may be used as provided herein are L-DNA (the backbone enantiomer of DNA, known in the literature), peptide nucleic acids (PNA) bisPNA clamp, a pseudocomplementary PNA, a locked nucleic acid (LNA), or co-nucleic acids of the above such as DNA-LNA co-nucleic acids. It is to be understood that nucleic acids used as provided herein may be homogeneous or heterogeneous in nature. As an example, they may be completely DNA in nature or they may comprise DNA and non-DNA (e.g., LNA) monomers or sequences. Thus, any combination of nucleic acid elements may be used. The nucleic acid modification may render the nucleic acid more stable and/or less susceptible to degradation under certain conditions. For example, in some instances, the nucleic acids are nuclease-resistant.

Methods of synthesizing nucleic acids (e.g., ssDNA or dsDNA, or ssRNA or dsRNA) are known in the art and are described, for example, in U.S. Pat. Nos. 5,143,854 and 5,445,934, herein incorporated in their entirety.

Nucleic acids may be synthesized in vitro. Methods for synthesizing nucleic acids, including automated nucleic acid synthesis, are also known in the art. Nucleic acids having modified backbones, such as backbones comprising phosphorothioate linkages, and including those comprising chimeric modified backbones may be synthesized using automated techniques employing either phosphoramidate or H-phosphonate chemistries. (F. E. Eckstein, "Oligonucleotides and Analogues—A Practical Approach" IRL Press, Oxford, UK, 1991, and M. D. Matteucci and M. H. Caruthers, *Tetrahedron Lett.* 21, 719 (1980)) Aryl- and alkylphosphonate linkages can be made, e.g., as described in U.S. Pat. No. 4,469,863; and alkylphosphotriester linkages (in which the charged oxygen moiety is alkylated), e.g., as described in U.S. Pat. No. 5,023,243 and European Patent No. 092,574, can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165; Crooke S T et al. (1996) Annu Rev Pharmacol Toxicol 36:107-129; and Hunziker J et al. (1995) Mod Synth Methods 7:331-417.

Nucleic acids may additionally or alternatively comprise modifications in their sugars. For example, a β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, arabinose, 2'-F-arabinose, 2'-O—(C$_1$-C$_6$)alkyl-ribose, preferably 2'-O—(C$_1$-C$_6$)alkyl-ribose is 2'-O-methylribose, 2'-O—(C$_2$-C$_6$)alkenyl-ribose, 2'-[O—(C$_1$-C$_6$)alkyl-O—(C$_1$-C$_6$)alkyl]-ribose, 2'-NH$_2$-2'-deoxyribose, β-D-xylo-furanose, α-arabinofuranose, 2,4-dideoxy-β-D-erythro-hexo-pyranose, and carbocyclic (described, for example, in Froehler J (1992) Am Chem Soc 114:8320) and/or open-chain sugar analogs (described, for example, in Vandendriessche et al. (1993) Tetrahedron 49:7223) and/or bicyclosugar analogs (described, for example, in Tarkov M et al. (1993) Helv Chim Acta 76:481).

Nucleic acids may comprise modifications in their bases. Modified bases include modified cytosines (such as 5-substituted cytosines (e.g., 5-methyl-cytosine, 5-fluoro-cytosine, 5-chloro-cytosine, 5-bromo-cytosine, 5-iodo-cyto sine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1, 2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'-β-D-2'-deoxyribofuranosyl)-2(1H)-pyridone, and its Watson-Crick complement dP, the purine analog, is 2-amino-8-(1'-β-D-1'-deoxyribofuranosyl)-imidazo[1,2-a]-1,3,5-triazin-4(8H)-one.

In exemplary embodiments, nucleic acid nanostructures comprise single-stranded genomic DNA. For example, nucleic acid nanostructures may comprise linear or circular single-stranded M13 plasmid DNA. In some embodiments, nucleic acid nanostructures do not comprise plasmid DNA.

It should be appreciated that nucleic acid nanostructures of the present disclosure, in some embodiments, do not include condensed nucleic acid. As used herein, "condensed nucleic acid" refers to compacted nucleic acid, for example, that is twisted and coiled upon itself (see, e.g., Teif VB, et al. *Progress in Biophysics and Molecular Biology* 105 (3): 208-222, incorporated by reference herein). The term "condensed nucleic acid" excludes nucleic acid nanostructures that have a distinct 2D or 3D architecture.

It should also be appreciated that nucleic acid nanostructures of the present disclosure, in some embodiments, do not include coding nucleic acid. That is, in some embodiments, nucleic acid nanostructures comprise non-coding nucleic acids (e.g., nucleic acids that do not encode proteins). As used herein, a "coding nucleic acid" refers to a nucleic acid containing a nucleotide sequence that specifies a sequence of amino acids of a protein (e.g., a therapeutic protein). Thus, a "non-coding nucleic acid" is a nucleic acid that does not specify a sequence of amino acids of a protein and, accordingly, is not transcribed into RNA or translated into protein. In other embodiments, it should be understood that a nucleic acid nanostructure may contain one or more coding nucleic acids.

In some embodiments, nucleic acids used to make nucleic acid nanostructures do not code for any amino acid. In some embodiments, nucleic acids used to make nucleic acid nanostructures do not code for more than 1, 2, 3, 4 or 5 consecutive amino acids.

In some embodiments, nucleic acids used to make nucleic acid nanostructures do not include art-recognized regulatory elements/sequences such as promoters, enhancers, polyA sequences and/or ribosomal binding site sequences.

In some embodiments, nucleic acids used to make nucleic acid nanostructures are not plasmids.

In some embodiments, nucleic acids used to make nucleic acid nanostructures contain more than one nucleic acid, and the nucleic acid are different from each other. That is, the nucleic acids of a nucleic acid nanostructure may comprise a plurality of different nucleic acids.

In some embodiments, nucleic acid nanostructures are not encapsulated by or coated with (e.g., linked to) lipids. For example, a variety of gene delivery methods of the prior art make use of nucleic acid nanostructures that are linked to hydrophobic moieties and/or covered by lipids (e.g., such as a lipid bilayer), which function to prevent nuclease degradation (see, e.g., WO 2013148186 A1). The present disclosure, in some embodiments, excludes nucleic acid nanostructures that are linked to hydrophobic moieties and/or covered by lipids. In other embodiments, however, a nucleic acid nanostructure may contain one or more nucleic acids linked to one or more hydrophobic moieties and/or lipids.

Nucleic acid nanostructures of the present disclosure have a variety of in vitro and in vivo uses. In some embodiments, may be used as scaffolds, cages or multifunctional carriers for delivering an antigen that is intended for use in vivo and/or in vitro. A nucleic acid nanostructure may be delivered by any suitable delivery method, for example, intravenously or orally.

The present disclosure contemplates imparting addressability to nucleic acid nanostructures. For example, nucleic acid nanostructures may be modified by site-specific attachment of targeting moieties such as proteins, ligands or other small biomolecules. In some embodiments, nucleic acid nanostructures may comprise nucleic acid "staple" strands, as described above, that serve as handles for nanometer-specific placement of accessory molecules (e.g., biotin/streptavidin) at virtually any position on or within the structure (see, e.g., Stein et al. *Chemphyschem.* 12(3), 689-695 (2011); Steinhauer et al. *Angew Chem. Int. Ed. Engl.* 48(47), 8870-8873 (2009); Stein et al. *J. Am. Chem. Soc.* 133(12), 4193-4195 (2011); Kuzyk et al. *Nature* 483(7389), 311-314 (2012); and Ding et al. *J. Am. Chem. Soc.* 132(10), 3248-3249 (2010); Yan et al. *Science* 301(5641), 1882-1884 (2003); and Kuzuya et al. *Chembiochem.* 10(11), 1811-1815 (2009), each of which is incorporated by reference herein).

In some embodiments, nucleic acids of nanostructures provided herein may be modified (e.g., covalently modified) with a linker (e.g., biotin linker) during synthesis or via enzymatic means (see, e.g., Jahn et al. *Bioconjug. Chem.* 22(4), 819-823 (2011) incorporated by reference herein). Such methods may also be used to position reaction systems on nucleic acid nanostructures through the chemical biotinylation of enzyme molecules (see, e.g., Voigt et al. *Nat. Nanotechnol.* 5(3), 200-203 (2010)).

A more generalized antibody-based binding approach may also be used to link target proteins to nucleic acid nanostructures at defined distances (see, e.g., Williams et al. *Angew Chem. Int. Ed. Engl.* 46(17), 3051-3054 (2007); and He Y et al. *J. Am. Chem. Soc.* 128(39), 12664-12665 (2006), each of which is incorporated by reference herein). Thus, in some embodiments, nucleic acid nanostructures may be linked to one or more antibodies.

In other embodiments, DNA aptamers, which adopt a specific secondary structure with high binding affinity for a particular molecular target, may be used as linkers, thereby eliminating the need for protein linkers (see, e.g., Ellington et al. Nature 346(6287), 818-822 (1990); Chhabra et al. *J. Am. Chem. Soc.* 129(34), 10304-10305 (2007); and Rinker et al. *Nat. Nanotechnol.* 3(7), 418-422 (2008), each of which is incorporated by reference herein).

The present disclosure also contemplates the use of recombinant genetic engineering methods to selectively add affinity tags or other peptide linkers to nucleic acid nanostructures. For example, polyhistidine sequence consisting of multiple histidine residues on the C- or N-terminus end of a target protein is a commonly used tag for affinity-based purification. This, in turn, can be linked via nickel-mediated interaction to a nitrilotriacetic acid molecule that is covalently conjugated to an amine (see, e.g., Goodman et al. *Chembiochem.* 10(9), 1551-1557 (2009), incorporated by reference herein) or thiol-modified (see, e.g., Shen et al. *J. Am. Chem. Soc.* 131(19), 6660-6661 (2009), incorporated by reference herein) nucleic acid. Through this method, fluorescent proteins may be positioned both periodically and specifically on nucleic acid nanostructures (Goodman et al. (2009); and Shen et al. (2009)). Similarly, SNAP and HaloTag® peptide sequences, also used for affinity purification of recombinant proteins, may be utilized for the orthogonal decoration of nucleic acid nanostructures with different protein or enzyme species (see, e.g., Sacca et al. *Angew Chem. Int. Ed. Engl.* 49(49), 9378-9383 (2010), incorporated by reference herein). A related approach involving the creation of chimeric proteins conjugated to a DNA-binding domain, can eliminate the often complex chemical synthesis techniques and toxic compounds (e.g., nickel) necessary to stably conjugate affinity tag binding partners to oligonucleotide strands. Further, zinc-finger domains that recognize specific double-stranded sequences may be used to arrange fluorescent proteins at specific locations on nucleic acid nanostructures of the present disclosure (see, e.g., Nakata et al. *Angew Chem. Int. Ed. Engl.* 51(10), 2421-2424 (2012), incorporated by reference herein).

An adjuvant (e.g., CpG) and/or antigen may be covalently or non-covalently attached to a nucleic acid nanostructure. The location and nature of the linkage between the adjuvant (e.g., CpG) and/or antigen and the nucleic acid nanostructure will depend upon the function of the adjuvant (e.g., CpG) and/or antigen. As an example, an adjuvant (e.g., CpG) and/or antigen may be intended to release (including slow release) from the nanostructure, and in that case, the linkage between the adjuvant (e.g., CpG) and/or antigen and the nanostructure may be chosen to achieve the desired release profile. In some embodiments, an adjuvant (e.g., CpG) and/or antigen may be inactive in its bound form and activated only when released.

In some embodiments, an adjuvant (e.g., CpG) and/or antigen may be combined with nucleic acids during assembly (e.g., self-assembly) of nanostructures, or an adjuvant CpG) and/or antigen may be combined with pre-
formed nucleic acid nanostructures.

Adjuvant (e.g., CpG) and/or antigen may be linked to an
interior surface (in the interior compartment) or an exterior
surface of a nanostructure. Adjuvant (e.g., CpG) and/or
antigen may be arranged in various configurations. Upon
hybridization of handles to anti-handles, adjuvant (e.g.,
CpG) and/or antigen become indirectly linked to nucleic
acid nano structures. It should be understood that nanostruc-
tures of the present disclosure permit precise placement of
an adjuvant (e.g., CpG) and/or antigen or more than one
adjuvant (e.g., CpG) and/or antigen (e.g., a combination of
different adjuvant (e.g., CpG) and/or antigen) on the interior
and/or exterior surface of the nanostructures.

Nucleic acid nanostructures of the present disclosure
permit high-density "packing" of adjuvant (e.g., CpG) and/
or antigen on and into the nanostructures. In some embodi-
ments, a nucleic acid nanostructures is decorated with one
adjuvant (e.g., CpG) and/or antigen per 50 nm$^2$ to 75 nm$^2$.
In some embodiments, a nucleic acid nanostructure is deco-
rated with one adjuvant (e.g., CpG) and/or antigen per 50
nm$^2$, 55 nm$^2$, 60 nm$^2$, 65 nm$^2$, 70 nm$^2$ or 75 nm$^2$. For
example, using a rhombic-lattice spacing for a 30 nm tall, 60
nm diameter cylindrical nanostructure, 72 positions on the
exterior of the nanostructure and 84 positions on the interior
may be occupied by adjuvant (e.g., CpG) and/or antigen. For
larger nanostructures, for example, those with two 30
nm×60 nm cylindrical nanostructures, the number of posi-
tions occupied by adjuvant (e.g., CpG) and/or antigen is
doubled. For even larger nanostructures, for example, those
with three 30 nm×60 nm cylindrical nanostructures, the
number of positions occupied by adjuvant (e.g., CpG) and/or
antigen tripled, and so on.

The present disclosure contemplates, in some aspects, the
delivery of nucleic acid nanostructures, or nucleic acid
nanostructures loaded with an adjuvant (e.g., CpG) and/or
antigen, systemically or to localized regions, tissues or cells.
Any adjuvant (e.g., CpG) and/or antigen gent may be
delivered using the methods of the present disclosure pro-
vided that it can be loaded onto or into the nucleic acid
nanostructure. Because such processes are relatively innocu-
ous, it is expected that virtually any adjuvant (e.g., CpG)
and/or antigen may be used.

The length of a CpG adjuvant may vary. For example, the
length may be 10-100 nucleotides (nt), 10-50 nt, or 10-20 nt.

Adjuvants

An "adjuvant" is an agent that enhances an immune
response to an antigen. In some embodiments, an adjuvant
is a CpG oligonucleotide. CpG oligonucleotides are short
single-stranded synthetic DNA molecules that contain a
cytosine triphosphate deoxynucleotide ("C") followed by a
guanine triphosphate deoxynucleotide ("G"). The "p" refers
to the phosphodiester, or modified phosphorothioate (PS),
linkage between consecutive nucleotides. CpG oligonucle-
otides typically enhance the immunostimulatory effect of
nucleic acid nanostructures (Li, J. et al. ACS NANO, 5(11):
8783-8789, 2011; Schuller, V. et al. ACS NANO, 5(12):
9696-9702, 2011). For example, after they are taken up by
cells, CpG oligonucleotides, which are a hallmark of micro-
bial DNA, are recognized by the endosomal Toll-like recep-
tor 9 (TLR9) that activates downstream pathways to induce
immunostimulatory effects, producing high-level secretion
of various pro-inflammatory cytokines including tumor
necrosis factor (TNF)-α, interleukin (IL)-6, and IL-12. In
some embodiments, CpG oligonucleotides are linked to an
interior surface of a nucleic acid nanostructure. In some
embodiments, CpG oligonucleotides are linked to an exterior surface of a nucleic acid nanostructure. In some embodi-
ments, a nucleic acid nanostructure has CpG oligonucle-
otides linked to both an interior and exterior surface. Other
examples of adjuvants include, without limitation, lipopo-
lysaccharide and polyI:C (dsRNA mimic).

A "subject" to which administration is contemplated
includes, but is not limited to, humans (e.g., a male or female
of any age group, e.g., a pediatric subject (e.g., infant, child,
adolescent) or adult subject (e.g., young adult, middle-aged
adult or senior adult)) and/or other non-human animals, for
example mammals (e.g., primates (e.g., cynomolgus mon-
keys, rhesus monkeys), including commercially relevant
mammals such as cattle, pigs, horses, sheep, goats, cats,
and/or dogs), birds (e.g., commercially relevant birds such
as chickens, ducks, geese, and/or turkeys), reptiles, amphib-
ians, and fish. In some embodiments, the non-human animal
is a mammal. The non-human animal may be a male or
female and at any stage of development. A non-human
animal may be a transgenic animal.

Nucleic acid nanostructures and compositions containing
nucleic acid nanostructures may be administered to a subject
(e.g., a human or non-human subject) subcutaneously or
intravenously (e.g., single/multiple injection(s) or continu-
ous infusion), or by other means.

In some embodiments, nucleic acid nanostructures are
administered to a subject as a component of a polymeric gel
composition. The polymeric gel composition may be bio-
compatible and/or biodegradable. In some embodiments, the
polymeric gel composition is formed from, and/or comprises
at least one polylactic acid, polyglycolic acid, PLGA poly-
mers, alginates and alginate derivatives, gelatin, collagen,
agarose, natural and synthetic polysaccharides, polyamino
acids such as polypeptides particularly poly(lysine), poly-
esters such as polyhydroxybutyrate and poly-epsilon-capro-
lactone, polyanhydrides; polyphosphazines, poly(vinyl alco-
hols), poly(alkylene oxides) particularly poly(ethylene
oxides), poly(allylamines)(PAM), poly(acrylates), modified
styrene polymers such as poly(4-aminomethylstyrene),
pluronic polyols, polyoxamers, poly(uronic acids), poly
(vinylpyrrolidone) and copolymers of the above, including
graft copolymers (see, e.g., International Publication No.
WO2009102465).

In some embodiments, the present disclosure provides
methods for manipulating, directly in the body, dendritic-
cell recruitment and activation. Immature dendritic cells
patrol peripheral tissues, and on uptake of foreign sub-
stances (e.g., antigen), they may mature to express on their
surface molecules (e.g., the receptor CCR7 and major his-
tocompatibility complex (MHC) antigen) to facilitate
lymph-node homing and subsequent antigen presentation to
T-cells, respectively. Elements of infection that mobilize and
activate dendritic cells include inflammatory cytokines, and
"danger signals" related specifically to the infectious agent.
Cytosine-guanosine oligonucleotide (CpG-ODN) sequences
are uniquely expressed in bacterial DNA, and are potent
danger signals that stimulate mammalian dendritic-cell acti-
vation and dendritic-cell trafficking. Thus, in some embodi-
ments, the present disclosure provides methods for admin-
istering to a subject nucleic acid nanostructures that
comprise antigen (e.g., cancer antigen) and danger signals
(e.g., CpG oligonucleotides).

Antigens

An "antigen", as used herein, may refer to any biomol-
ecule that may induce an immune response. In some
embodiments, an antigen is a peptide, a protein or polypep-
tide, or a nucleic acid. In some embodiments, an antigen is
a cancer antigen. A cancer antigen may be a component or element of a cancer cell or a biomolecule isolated from a cancer cell (e.g., a biomolecule known to be associated with cancerous tumors). In some embodiments, a cancer antigen comprises a biomolecule (e.g., a peptide or polypeptide) that is overexpressed or overactivated in cancer cells, relative to normal and non-cancerous cells.

Non-limiting examples of cancer antigens include Her2 peptides (for vaccination against selected breast cancers); NY-ESO-1 peptides (for vaccination against selected bladder cancers); HPV16 E7 peptides (for vaccination against selected cervical cancers); carcinoembryonic antigen (for vaccination against selected colorectal cancers); Wilms' tumor 1 (WT1) peptides (for vaccination against selected leukemias); MART-1, gp100, and tyrosinase (for vaccination against selected melanomas); URLC10, VEGFR1, and VEGFR2 (for vaccination against selected non-small lung cell cancers); survivin (for vaccination against selected ovarian cancers); MUC1 (for vaccination against selected pancreatic cancers); MUC2 (for vaccination against selected prostate cancers); telomerase (TERT); Indoleamine 2,3-dioxygenase (IDO1); CTAG1B, and VEGF receptors (FLT1 and KDR). In some embodiments, a cancer antigen is as described in Tagliamonte, M. et al. "Antigen-specific vaccines for cancer treatment", Hum Vaccin Immunother. 2014 November; 10(11): 3332-3346.; or Pol, J. et al. "Trial Watch: Peptide-based anticancer vaccines", Oncoimmunology. 2015 April; 4(4): e974411.

In some embodiments, a cancer antigen is selected from the following: CEA; gp1OO; Pmell7; mammaglobin-A; Melan-A; MART-1; NY—BR-1; ERBB2; OA1; PAP; PSA; RAB38; NY-MEL-1; TRP-1; gp75; TRP-2; tyrosinase; WT1; CD33; BAGE-1; D393-CD20n; Cyclin-A1; GAGE-1,2,8; GAGE-3,4,5,6,7; GnTVf; HERV-K-MEL; KK-LC-1; KM-HN-1; LAGE-1; LY6K; MAGE-A1; MAGE-A2; MAGE-A3; MAGE-A4; MAGE-A6; MAGE-A9; MAGE-A10; MAGE-A12m; MAGE-C1; MAGE-C2; mucink; NA88-A; NY-ESO-1; LAGE-2; SAGE; Spl7; SSX-2; SSX-4; survivin; BIRC5; TAG-1; TAG-2; TRAG-3; TRP2-INT2g; XAGE-1b; GAGED2a; BCR-ABL (b3a2); adipophilin; AIM-2; ALDH1A1; BCLX(L); BING-4; CALCA; CD45; CD274; CPSF; cyclin D1; DKK1; ENAH (hMena); EpCAM; EphA3; EZH2; FGF5; glypican-3; G250; MN; CAIX; HER-2; neu; HLA-DOB; Hepsin; IDO1; IGF2B3; IL13Ralpha2; Intestinal carboxyl esterase; alpha-foetoprotein; Kallikrein 4; KIF20A; Lengsin; M-CSF; MCSP; mdm-2; Meloe; Midkine; MMP-2; MMP-7; MUC1; MUC5AC; p53; PAX5; PBF; PRAME; PSMA; RAGE-1; RGSS; RhoC; RNF43; RU2AS; secernin 1; SOX10; STEAP1; Telomerase; TPBG; and VEGF.

Methods of Use

The nucleic acid nanostructures described herein (e.g., comprising antigen, CpG ligand, and/or oligolysine-PEG) may be used vaccines to induce an immune response to a particular antigen, such as a tumor antigen or a microbial (e.g., bacterial or viral) antigen.

In some embodiments, administration of the nanostructure results in an at least 2-fold or at least 3-fold reduction in tumor volume.

In some embodiments, administration of the nanostructure stimulates cytokine production in dendritic cells of the subject, wherein the cytokine production is at least 10%, at least 15%, or at least 20% higher than cytokine production by dendritic cells in a subject administered antigen only or antigen and free CpG oligonucleotides.

In some embodiments, administration of the nanostructure stimulates Interleukin-10 (IL10) production in dendritic cells of the subject. In some embodiments, administration of the nanostructure stimulates Interleukin-12 (IL12) production in dendritic cells of the subject.

In some embodiments, administration of the nanostructure increases antigen uptake in dendritic cells of the subject, wherein the antigen uptake is at least 10%, at least 15%, or at least 20% higher than antigen uptake by dendritic cells in a subject administered antigen only or antigen and free CpG oligonucleotides.

In some embodiments, administration of the nanostructure stimulates a stronger Th1 immune response, relative to stimulation of a Th2 response. The Th1 response stimulated may be at least 10%, at least 15%, at least 20%, at least 25%, at least 30%, at least 35%, at least 40%, at least 45%, or at least 50% stronger than a Th2 response stimulated by administration of the nanostructure.

In some embodiments, the Th1 immune response is characterized by expression of CD69 and CD8 on T cells. In some embodiments, the expression of CD69 and/or CD8 on T cells of a subject following administration of the nanostructure may be at least 10%, at least 15%, at least 20%, at least 25%, at least 30%, at least 35%, at least 40%, at least 45%, or at least 50% higher than expression of the same molecule in T cells of a subject administered a control (e.g., antigen only or antigen and free CpG oligonucleotides).

In some embodiments, administration of the nanostructure stimulates CD8+ T cell proliferation by at least 10%, at least 15%, or at least 20% relative to CD8+ T cell proliferation in control cells in a subject administered antigen only or antigen and free CpG oligonucleotides.

In some embodiments, administration of the nanostructure stimulates IFN-$\gamma$ expression in OT-I CD8+ T cells of the subject, wherein the IFN-$\gamma$ expression is at least 10%, at least 15%, or at least 20% higher than IFN-$\gamma$ expression by in OT-I CD8+ T cells in a subject administered antigen only or antigen and free CpG oligonucleotides.

Additional Embodiments

The present disclosure provides the following additional embodiments:

1. A nucleic acid nanostructure comprising a plurality of uniformly spaced CpG ligands and a plurality of antigens, wherein the nucleic acid nanostructure is coated and covalently crosslinked with oligolysine-polyethylene glycol (PEG) copolymer, optionally at a N:P (nitrogen in lysine to phosphorus in nucleic acid) ratio of 0.1:1 to 1:1.

2. The nucleic acid nanostructure of paragraph 1, wherein each CpG ligand of the plurality of CpG ligands is uniformly spaced 2 nm-10 nm (e.g., 2.5 nm, 3.5 nm, 5 nm or 7 nm) from any other CpG ligand, optionally wherein the nucleic acid nanostructure comprises 10-100 (e.g., 10-50 or 10-20) CpG ligands.

3. The nucleic acid nanostructure of paragraph 1, wherein each CpG ligand of the plurality of CpG ligands is uniformly spaced 3 nm-5 nm, 3 nm-4 nm, or 3.5 nm from any other CpG ligand.

4. A nucleic acid nanostructure comprising a plurality of CpG ligands and a plurality of antigens, wherein each CpG ligand of the plurality of CpG ligands is uniformly spaced 3 nm-5 nm, 3 nm-4 nm, or 3.5 nm from any other CpG ligand.

5. The nucleic acid nanostructure of paragraph 4, wherein the nucleic acid nanostructure is coated and covalently crosslinked with oligolysine-polyethylene glycol (PEG) copolymer.

6. The nucleic acid nanostructure of any one of paragraphs 1-5, wherein the nucleic acid nanostructure is a DNA origami nanostructure.

7. The nucleic acid nanostructure of paragraph 6, wherein the DNA origami nanostructure is a 126-helix DNA origami nanostructure.

8. The nucleic acid nanostructure of any one of paragraphs 1-7, wherein the plurality of antigens comprise ovalbumin.

9. The nucleic acid nanostructure of any one of paragraphs 1-8, wherein the plurality of antigens are covalently linked to the nanostructure.

10. The nucleic acid nanostructure of paragraph 9, wherein the plurality of antigens are covalently linked to free amine groups of the nucleic acid nanostructure.

11. A method of inducing a Th1 polarized immune response in cells, the method comprising administering to a subject the nucleic acid nanostructure of any one of paragraphs 1-10.

12. A method of inducing a Th1 polarized immune response in cells, the method comprising administering to a subject a nucleic acid nanostructure comprising a plurality of uniformly spaced CpG ligands and a plurality of antigens.

13. The method of paragraph 11 or 12 wherein the subject has a tumor (e.g., a cancerous tumor).

14. The method of paragraph 13, wherein the volume of the tumor is reduced at least 2-fold relative to control.

15. The method of paragraph 14, wherein the volume of the tumor is reduced at least 3-fold relative to control.

16. The method of any one of paragraphs 11-15, wherein the nucleic acid nanostructure is administered to the subject multiple times (e.g., at least 2 times, at least 3 times, etc.).

EXAMPLES

Example 1

Fabrication of Square-Lattice Blocks (SQBs) with Different CpG Spacing

Using scaffold p8634 as template, the folding of SQBs with square-lattice blocks (comprising 126 helices) were designed using Cadnano software. One end of the helices was flat, while the other end of the helices had some extruding extra scaffold. See FIGS. 2A-2D. FIG. 2A includes representative images showing the 3D nanostructure of the SQBs. FIG. 2B shows representative TEM images of SQB nanostructures folded at a 80-5040-18 temperature ramp. Eight (8) Cy5 fluorophores were appended to the extruding side through anti-handle strategy (FIG. 2C). Multi sides and size of the SQB DNA origami corresponding to the Cadnano 3D cartoon are depicted in the TEM images in FIG. 2D. The following four spacing strategies were designed, wherein two of the adjacent CpG sequences have a distance of 2.5 nm (CpG1), 3.5 nm (CpG2), 5 nm (CpG3) and 7 nm (CpG4) on the flat face of the helices, and 18 CpG sequences were applied (FIG. 2E).

Example 2

Different CpG-Cy5-SQBs Showed Concentration-Dependent Cellular Uptake by 293 T Cells and Mouse Bone Marrow Dendritic Cells (BMDCs)

Figure 3D:
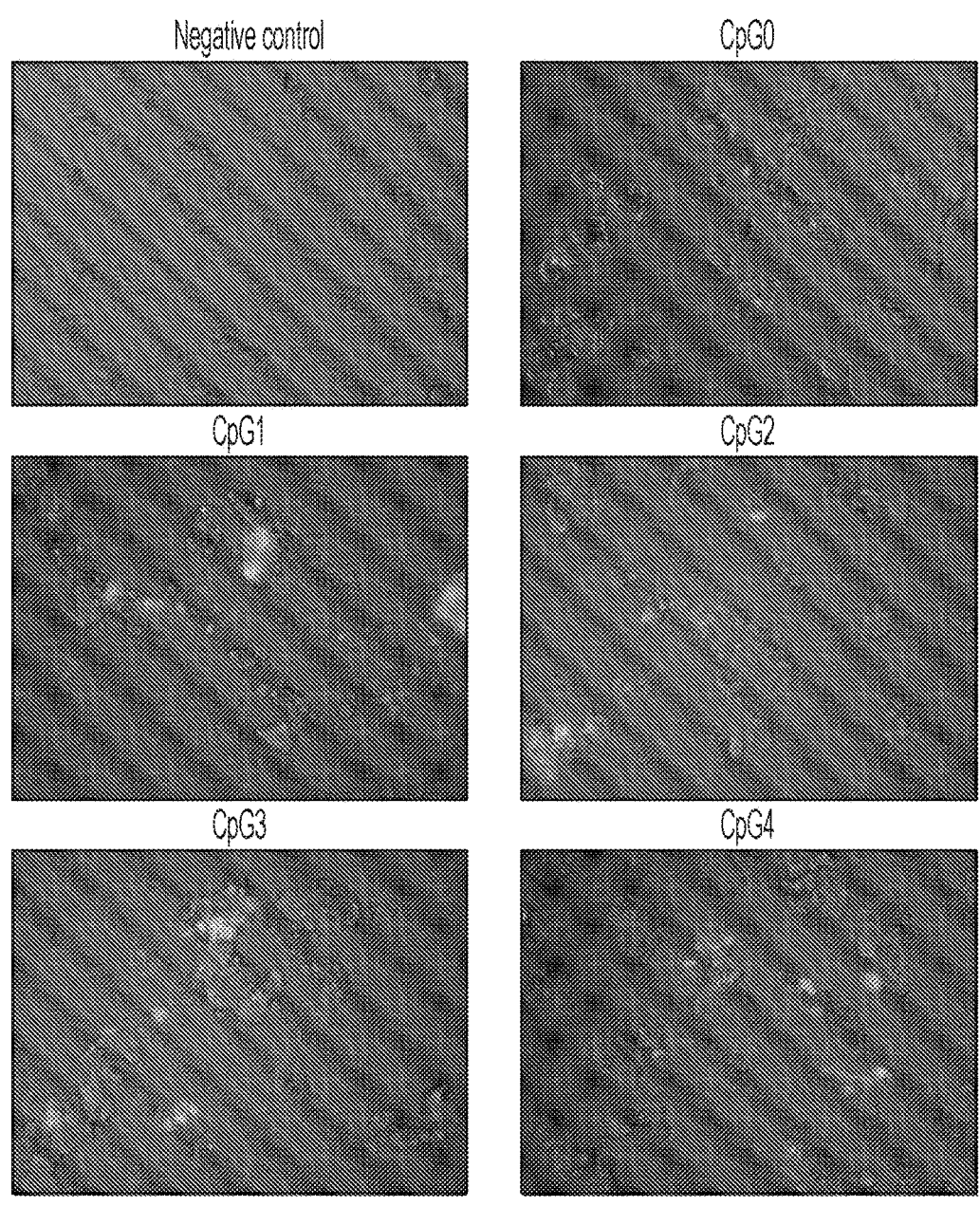
Figure 3E:
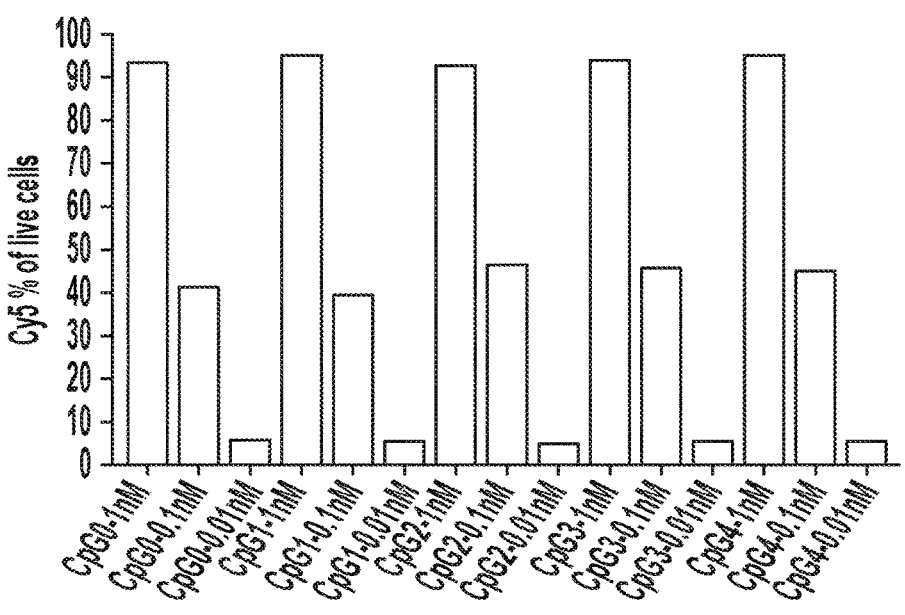
Figure 3F:
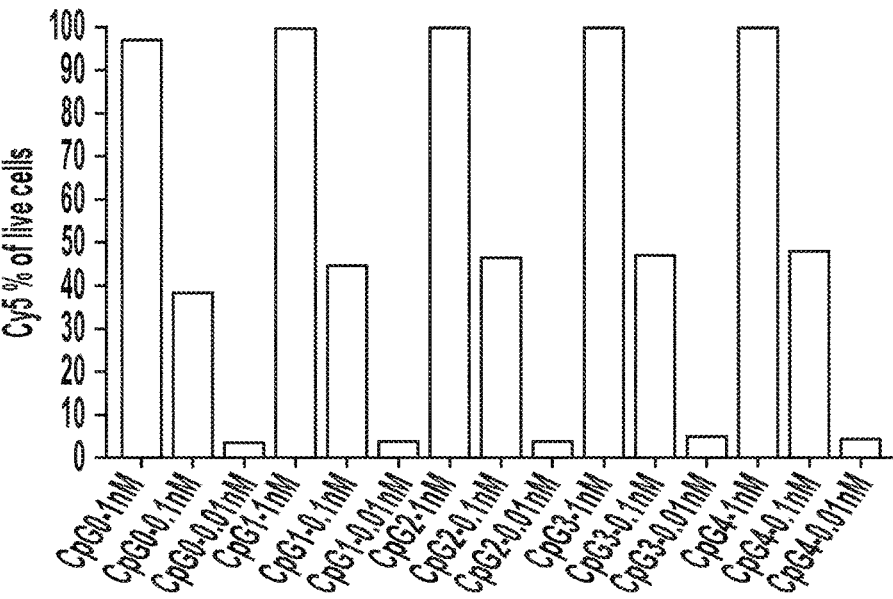

For cell uptake studies, polyethylene glycol (PEG) purification was first used to purify all the DNA origami nanostructures of Example 1 from extra staple strands (FIGS. 3A, 3B). The CpG0 DNA origami structures (no CpG ligand) were then coated with oligolysine-PEG (K10PEG5) and cultured in 10% fetal bovine serum (FBS) containing medium. the K10PEG5 stabilized the CpG0 DNA origami structures and protected them from denaturation induced by physiological salt concentrations and degradation mediated by nucleases (FIG. 3C). Three time points were assessed: culturing for 18 hours (h), 48 h, and 72 h. 293T cells and mouse bone marrow dendritic cells (BMDCs) were then transfected with 1 nm CpG-Cy5-SQBs (FIG. 3D). Dark coloration in the figures demonstrates presence of CpG-Cy5-SQBs. Flow cytometry data confirmed cell uptake by BMDCs when applying different concentration of CpG-Cy5-SQBs (FIGS. 3E, 3F). Thus, the K10PEG5-coated CpG-DNA nanostructures retained stability in the FBS-containing media and could be taken up by 293T cells and mouse BMDCs successfully.

Example 3

Dendritic Cell Maturation and Th1 Immune Response Polarization

Five (5) CpG-Cy5-SQBs were co-cultured with immature mouse BMDCs. Free CpG-ODN (200 nM P8634) was used as a positive control. It was found that BMDCs underwent severe apoptosis in the CpG-ODN control group compared to CpG-Cy5-SQB groups (FIGS. 4A, 4B). Interestingly, higher concentrations of CpG-Cy5-SQBs showed decreased cell apoptosis and cell death (FIG. 4B). Staining for DC maturation markers CD40 (FIG. 4C), CD80 (FIG. 4D), CD86 (FIG. 4E), MHC II (FIG. 4F) revealed that the CpG2 and CpG3 at spacing of 3.5 nm and 5 nm could greatly increase DC maturation signaling compared to CpG0. Through ELISA, it was found that CpG0 barely stimulates expression of IL-12 and IL-10 (indication of low immunogenicity of the origami), however, CpG2 could stimulate DCs to generate more IL-12 but less IL-10 (FIG. 4H). These results therefore suggest that CpG2 (spacing at 3.5 nm) favorably stimulate Th1 polarized immune responses which may greatly stimulate downstream Th1 CD4 cell and CD8 T cell activation.

Example 4

Antigen Uptake and Presentation

Figures 5A, 5B, 5C, 5D:
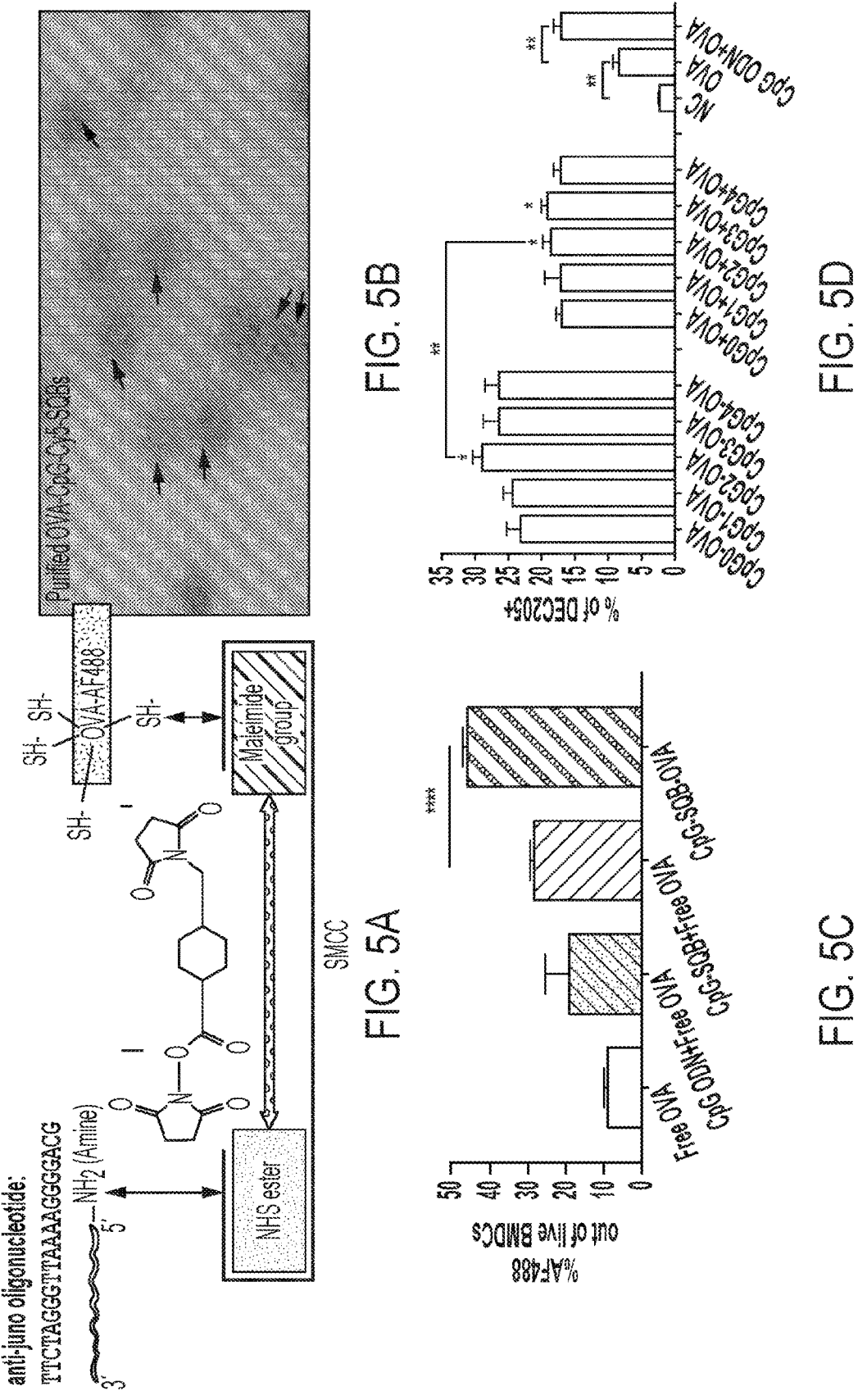

The model antigen OVA was conjugated to DNA origami as proof-of-concept for vaccine fabrication (FIG. 5A). OVA protein was observed on the extruding side of the SQBs by TEM image (FIG. 5B). By co-culturing with BMDCs, it was found that conjugated CpG-OVA greatly increased antigen uptake by BMDCs compared to same amount of free OVA with CpG-Cy5-SQBs or free CpG ODN (FIG. 5C). DEC-205 is reported be a marker of activated DCs involved in protein uptake. DEC205 was greatly increased in all the DNA origami groups when the antigen is co-delivered, especially in the CpG2 group, which likely contributes to increased antigen-uptake (FIG. 5D). Double positive population of CD86 and MHC DCs was significantly increased in CpG2 group (FIG. 5E). Similar results applied when single positive population was plotted. The presentation of OVA peptide SIINFEKL, an epitope presented by the mouse class I major histocompatibility, was significantly increased in all the origami vaccine applied groups, with CpG2 outperformed than all other versions (FIG. 5F). These data suggested that co-delivery of antigen and adjuvant is important for DC cell activation, and SQB nanoparticle might play an important role in MHC I cross-presentation pathway.

Example 5

Figures 6A, 6B, 6C, 6D:
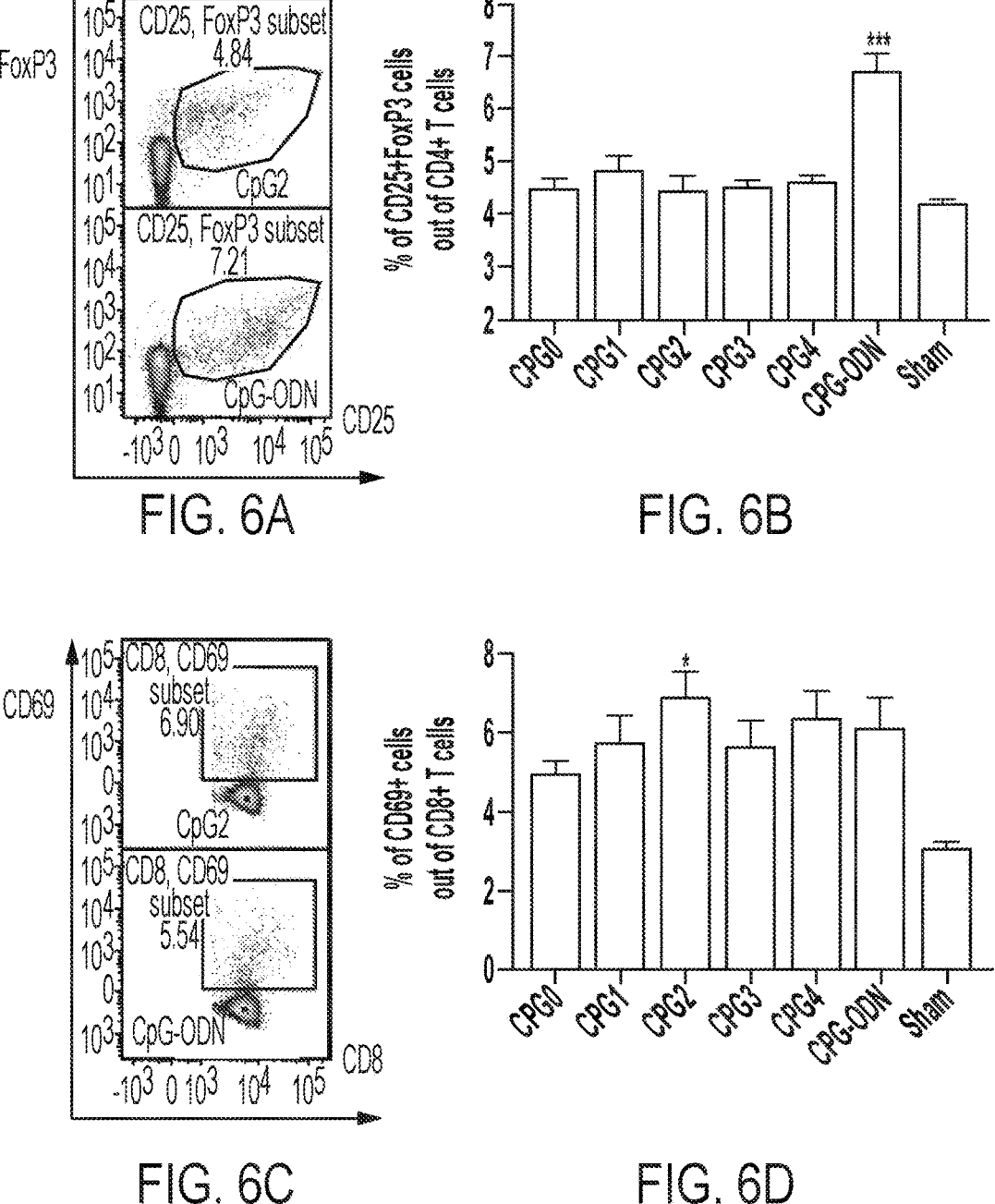
FIGS. 6A-6F include data showing that K10PEG5-coated CpG-DNA origami structures stabilize Tregs in the splenocyte while stimulating CD69 expression on CD8 T cells. See Example 5.
Figures 6E, 6F:
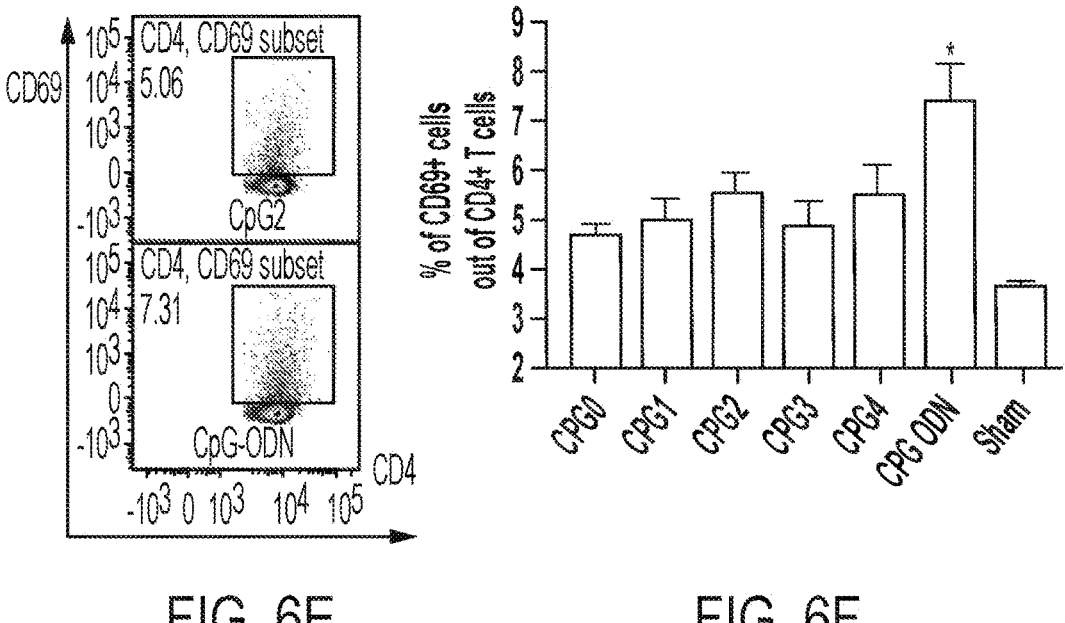

DNA Origami Stabilize Tregs in the Splenocyte While Stimulating CD69 Expression on CD8 T Cells Splenocytes were collected from C57BL/6 mouse and stimulated with different CpG-Cy5-SQBs. Naïve T cell early activation through cytokines secreted by DCs was observed. CD3+ T cells did not uptake the DNA origami structures (data not shown). Instead, Cy5 signal mostly existed in CD3− cells that might be DCs or macrophages. After two-day stimulation, it was found that CpG-Cy5-SQBs would not apparently increase suppressive FoxP3+CD25+ CD4+ Tregs compared to CpG-OND (FIGS. 6A, 6B). However, all the CpG-Cy5-SQBs could stimulate early activation marker CD69 expression on CD8+ and CD4+ T cells (FIGS. 6C, 6D). CpG2 groups showed enhanced expression of CD69+CD8+ T cells compared to CpG0. However, CpG-OND could strongly stimulate expression of CD69+CD4+ T cells compared to CpG-Cy5-SQBs (FIGS. 6E, 6F) (N=7). CD69 is an early activation marker, involved in lymphocyte proliferation and also contributing to the differentiation of Treg cells. These results suggested that CpG-Cy5-SQBs might favorably stimulate Th1 immune response, which is indicated by CD8 early activation and un-upregulated Tregs, whereas CpG-ODN might stimulate a Th2 preferable response by upregulating Tregs, which is less appreciated in cancer immunotherapy.

Example 6

OT-I and OT-II T Cell Stimulation In Vitro and Tumor Cell Killing In Vitro

Figure 7A:
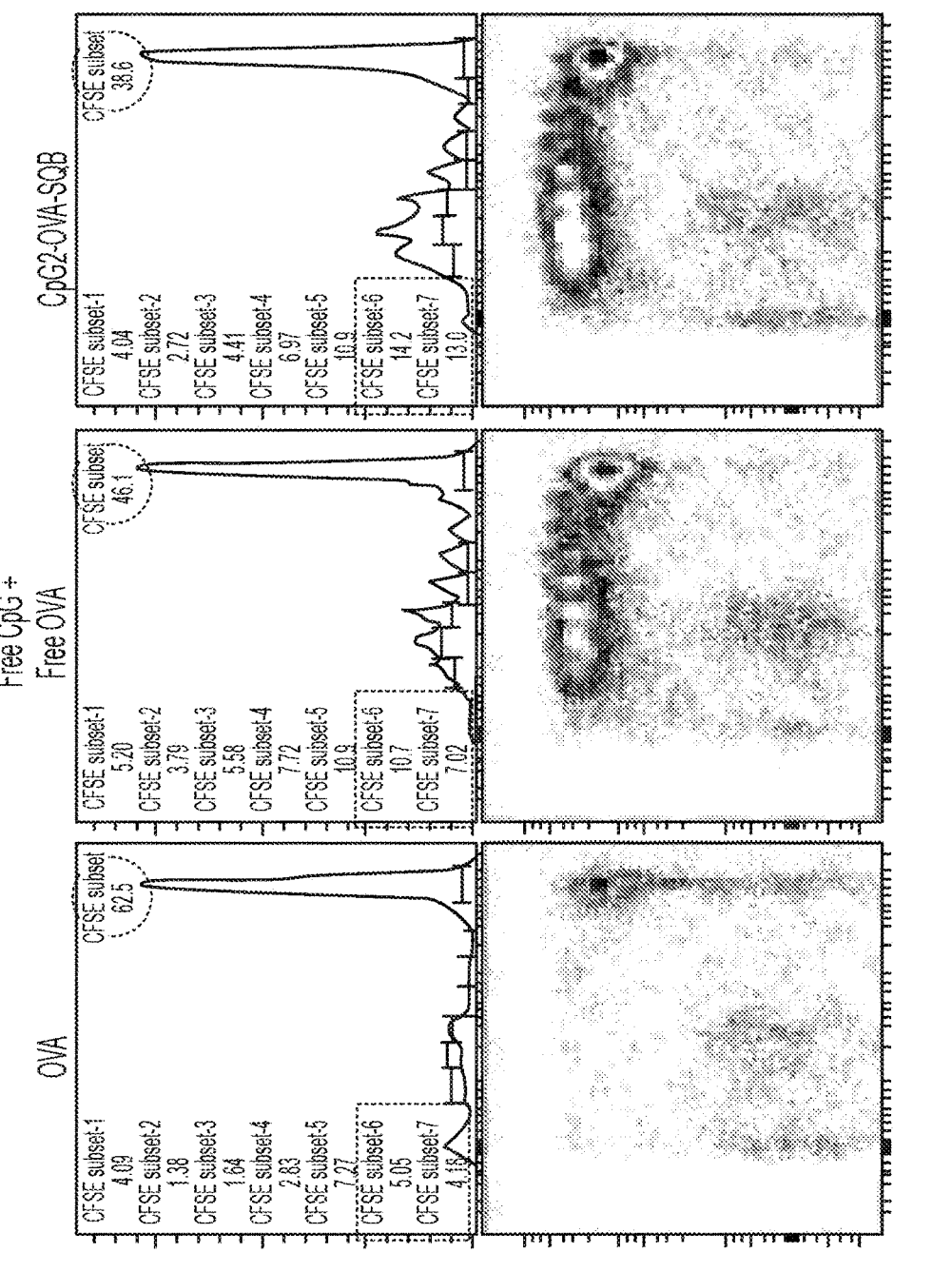
FIGS. 7A-7G includes data showing OT-I and OT-II T cell stimulation in vitro and tumor cell killing in vitro. See Example 6.
Figures 7B, 7C:
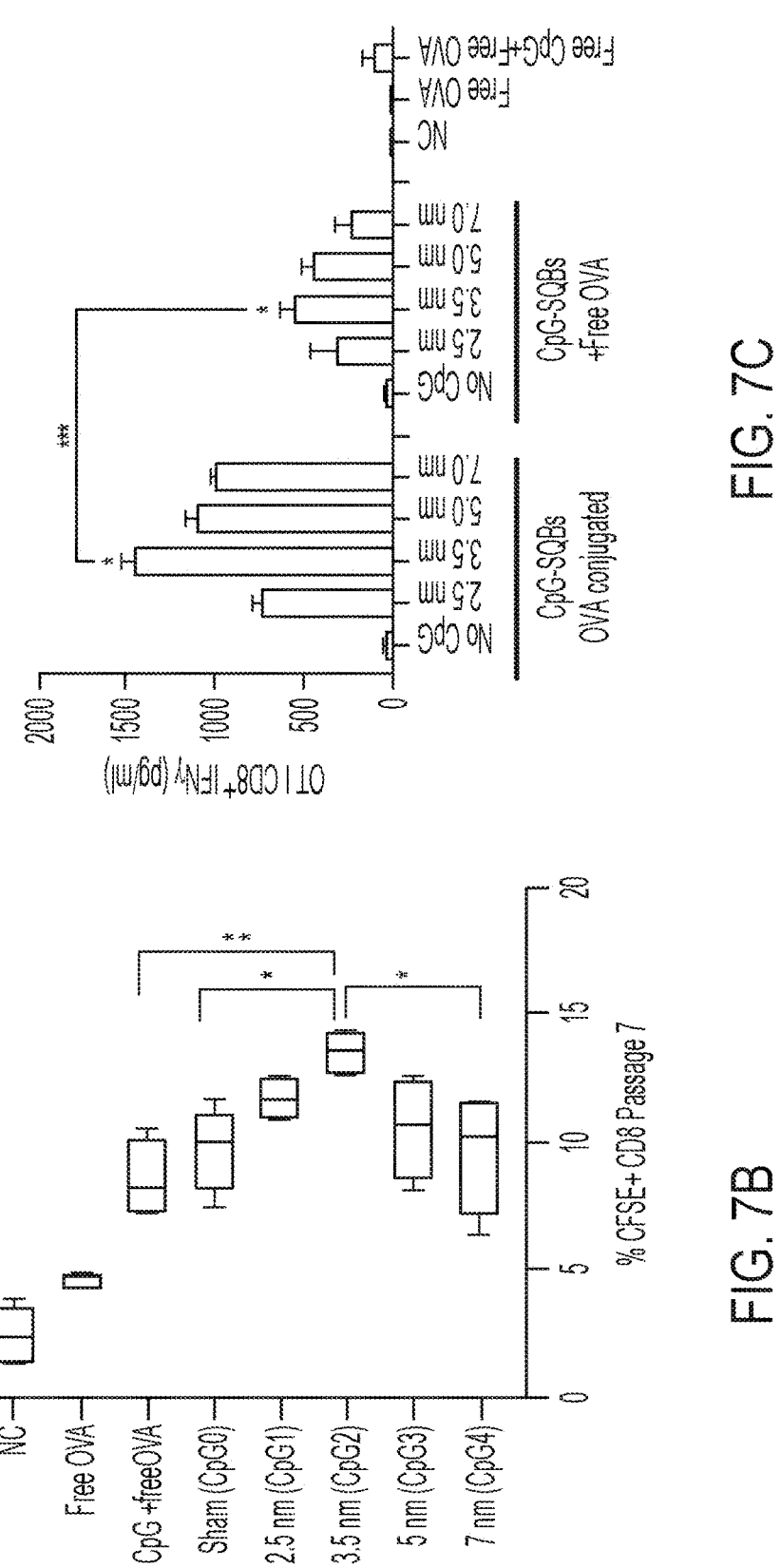
Figures 7D, 7E:
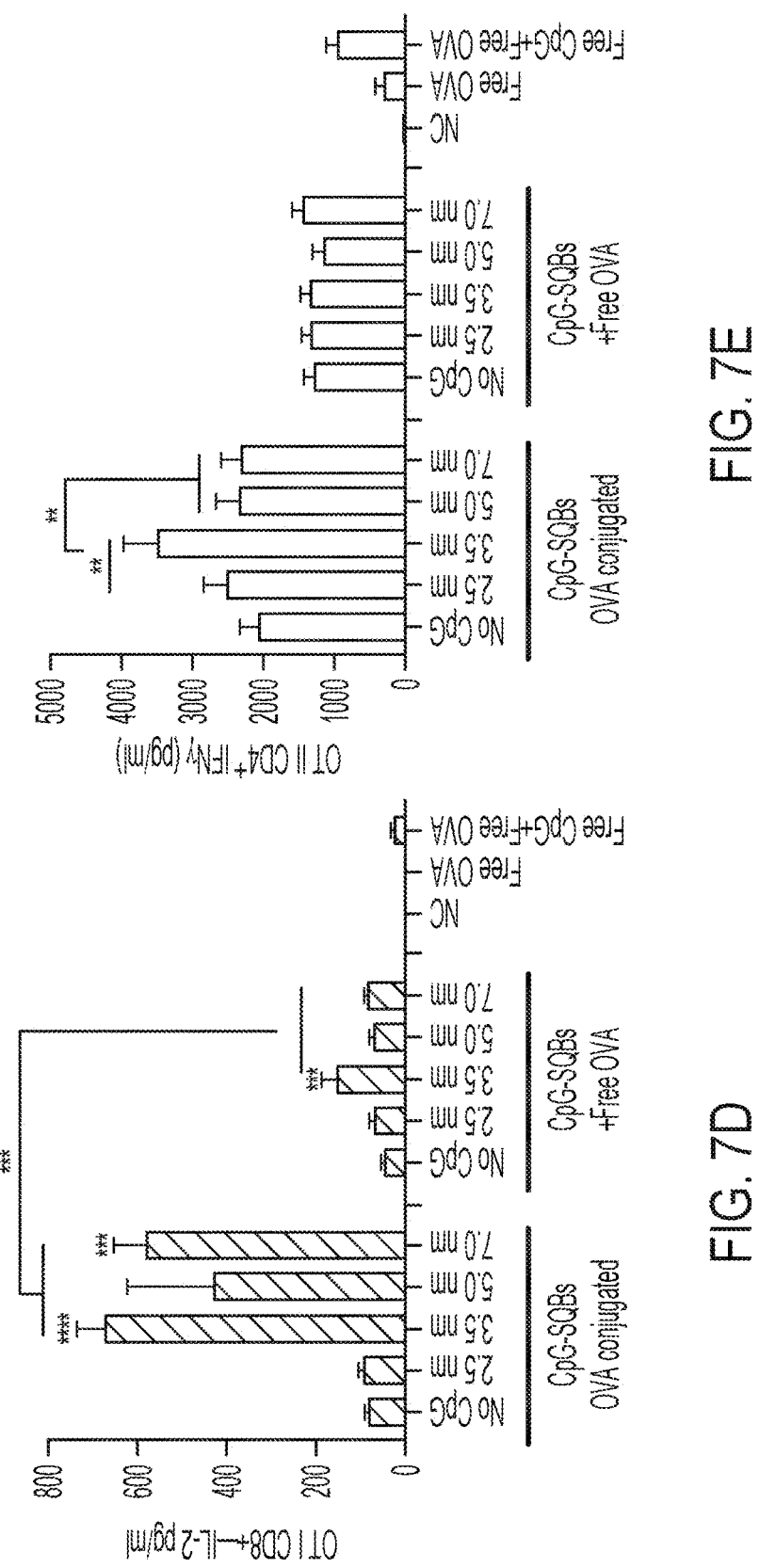
Figures 7F, 7G:
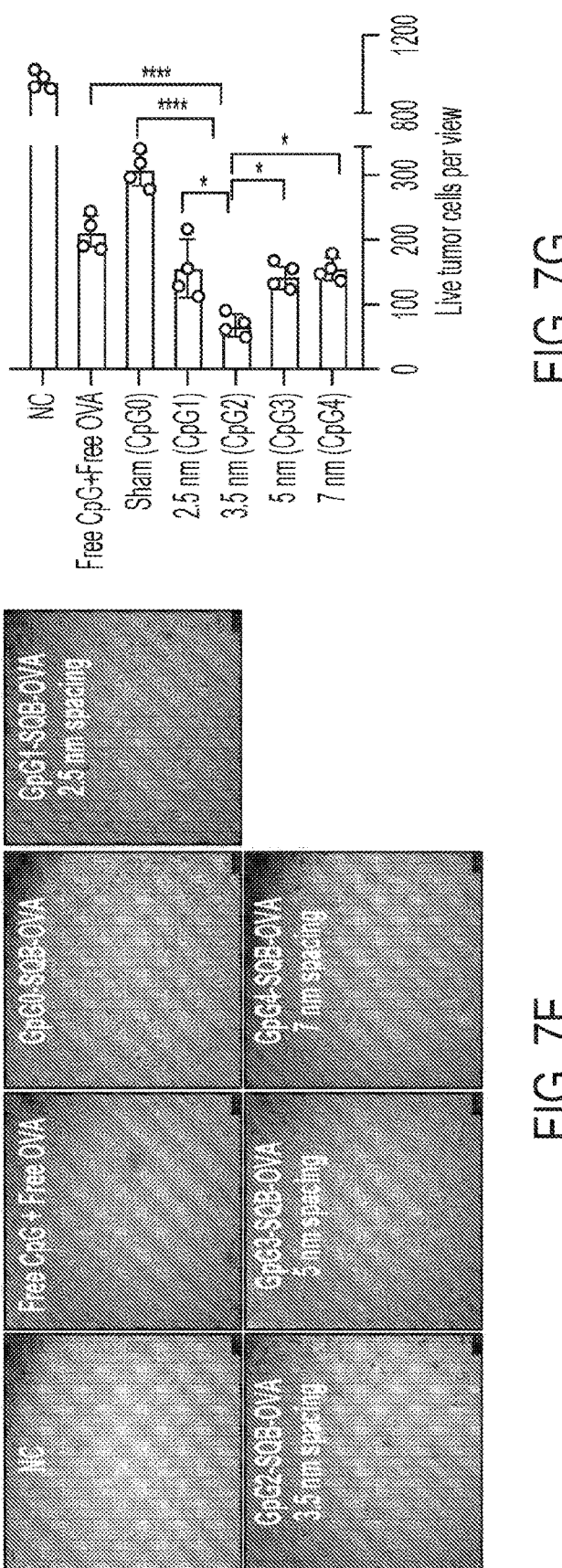

DNA origami vaccine pulsed DCs were cocultured with OT-I CD8+ T cells and OT-II CD4+ T cells. The results showed that CD8+ T cell proliferation was significantly increased in CpG2 (3.5 nm spacing) pulsed DC coculture group (FIGS. 7A, 7B). IFN-γ and that IL-2 expression on OT-I CD8+ T cells was strikingly increased in conjugated CpG-OVA-SQBs groups (FIGS. 7C, 7D), while the unconjugated counterpart only showed limited secretions. Especially CpG2 behaved better than other CpG spacings, indicating improved cross-presentation and CD8 proliferation. The results also showed that IFN-γ expression in OT-II CD4+ T cells was significantly increased in CpG2 group where antigen is co-delivered (FIG. 7C). In a tumor cell killing study, delivery of CpG2 (spacing at 3.5 nm) led to significant cell killing by activated CD8+ T cells (FIGS. 7F, 7G). These data suggest that: (1) co-presentation of antigen and adjuvant is important for effective DC stimulation, and DNA origami provides a superior platform for co-delivery that could improve antigen presentation by DCs and downstream Th1 polarization; and (2) antigen and adjuvant presentation together through DNA origami vaccine might preferentially increase MHC-I peptide presentation to OT-I T cells and increase CD8+ T cells proliferation and function.

Example 7

Control Spacing for CpG2

Figures 8A, 8B, 8C, 8D:
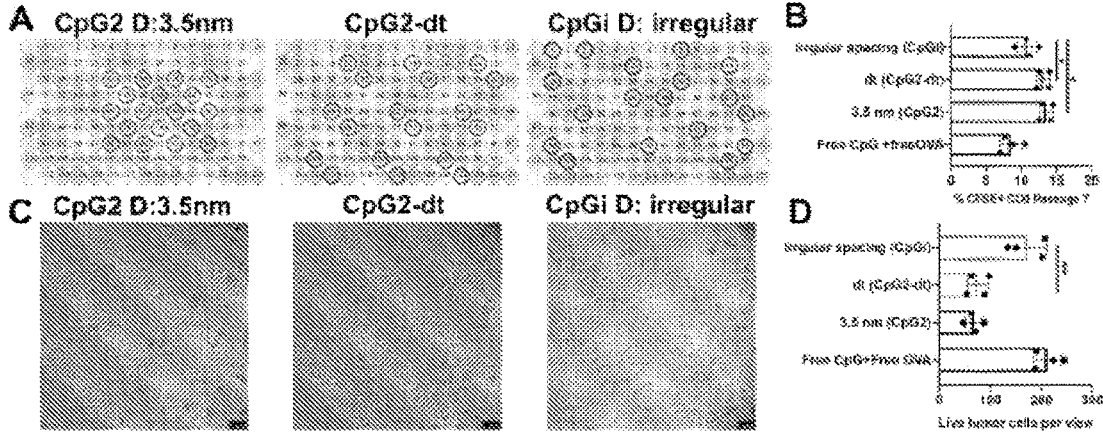
FIGS. 8A-8D show data relating to control spacing for CpG2. See Example 7.

To verify if a minimal CpG dimmer-trigger unit spacing at 3.5 nm is important for TLR9 dimerization and activation, CpG2-dt were designed with 9 pairs of dimmer-trigger units spaced out. Irregular spacing CpGi was also designed as positive control (FIG. 8A). The proliferation of CFSE positive OT-I CD8 T cells cocultured with pulsed DCs demonstrated that CpG2-dt seems to have similar stimulation effect compared to CpG2 (FIG. 8B). However, CpGi interrupted this effect. In the tumor cell-killing study, CpG2-dt showed similar results to CpG2, although CpG2 still showed the best tumor killing effects (FIG. 8C, D).

Example 8

Therapeutic and Prophylactic Effects in Mouse Melanoma Tumor Model

Figure 9G:
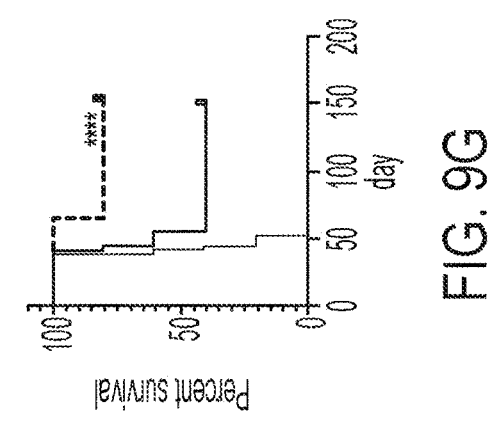
Figure 9F:
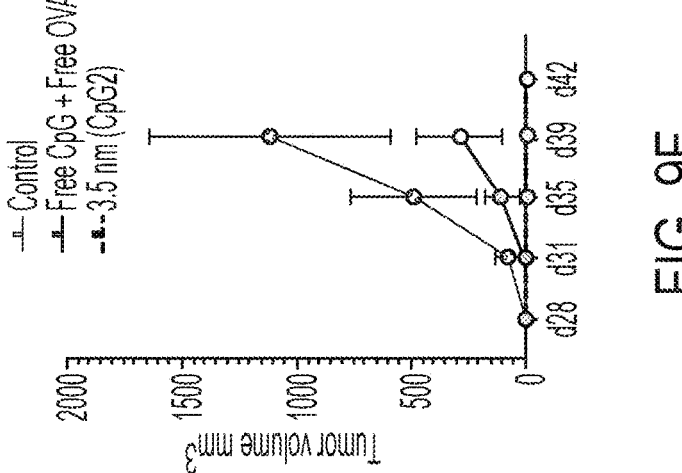
Figure 9E:
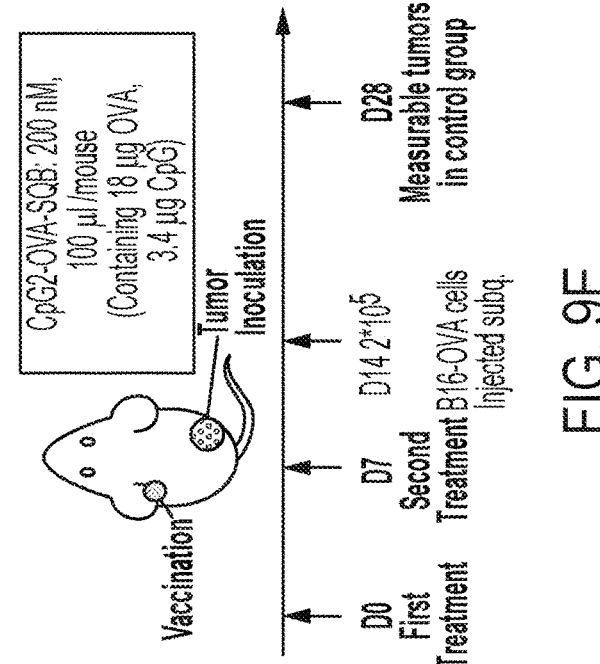

An aggressive melanoma mouse model was set up using 0.5 million B16-OVA cells. Three treatments of CpG2-OVA-SQBs vaccine were administered subcutaneously (FIG. 9A). Tumor growth was greatly inhibited compared to control free CpG+free OVA+free SQB applied groups and other spacing vaccines (FIGS. 9B, 9C). Note that the CpG and OVA administered were low doses compared to prior studies in the literature. In some mice, minimal tumor growth was noted as long as the treatment was given (FIG. 9B). Additionally, overall survival was greatly improved in the CpG2 vaccine applied group (FIG. 9D). In a prophylactic study, two doses of CpG2-OVA-SQBs were injected subcutaneously on day 1 and day 7, and then inoculated the mice with tumor cells (FIG. 9E). On day 28, measurable tumors were observed in control groups and in 40% of the free CpG and free OVA applied group (FIG. 9F). No tumors were observed in DNA origami vaccine treated group. All 5 mice in the control group had died by the conclusion of the study. 60% of mice in the free CpG and free OVA applied group had died. Only one mouse in CpG2-OVA-SQBs applied group was dead at the end point of the study (FIG. 9G). These results verified the effectiveness of the DNA origami vaccine in a murine melanoma model.

Example 9

Immune Cell Profiling in Animals Post Vaccination

Figures 10A, 10B, 10C, 10D:
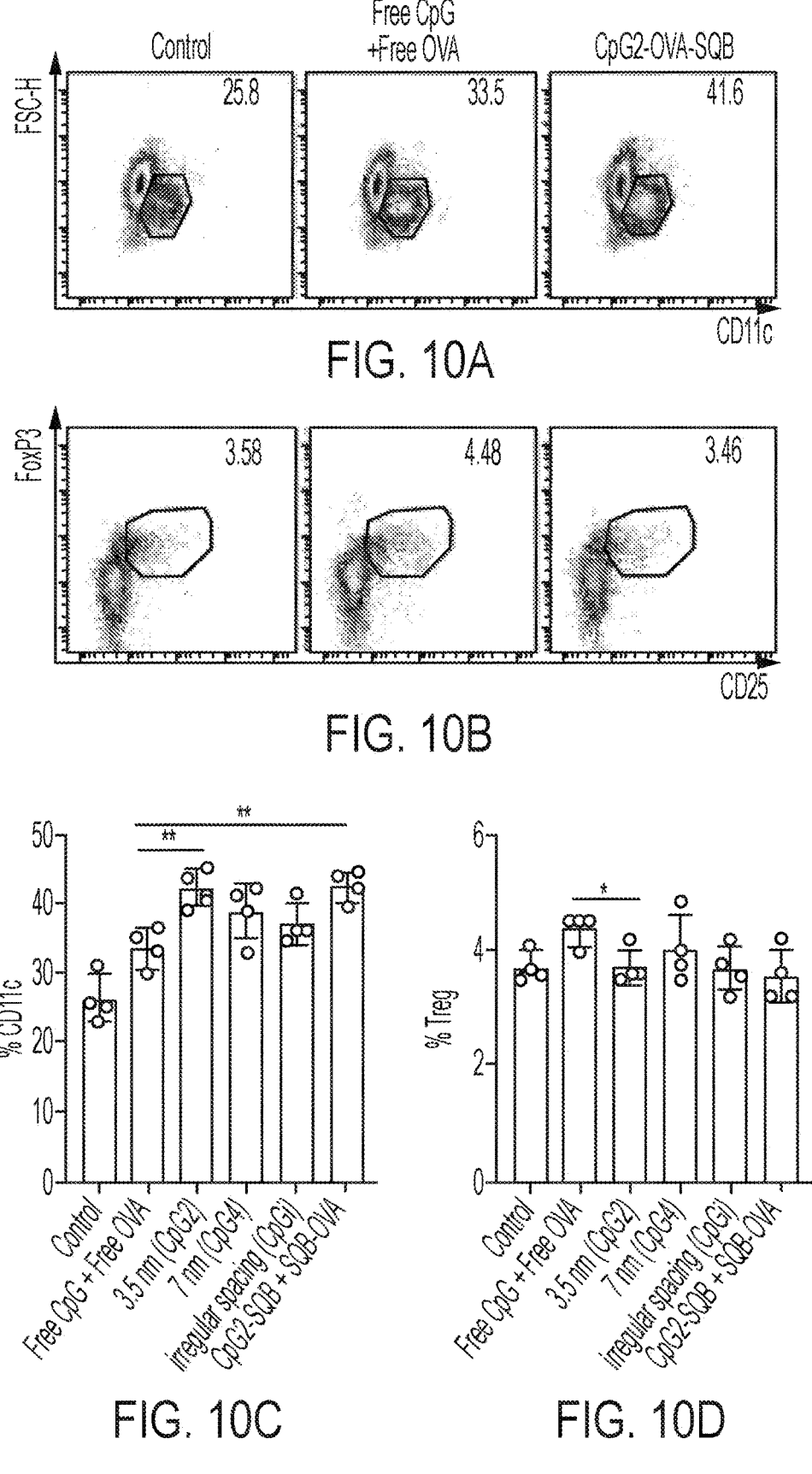
Figures 10E, 10F, 10G:
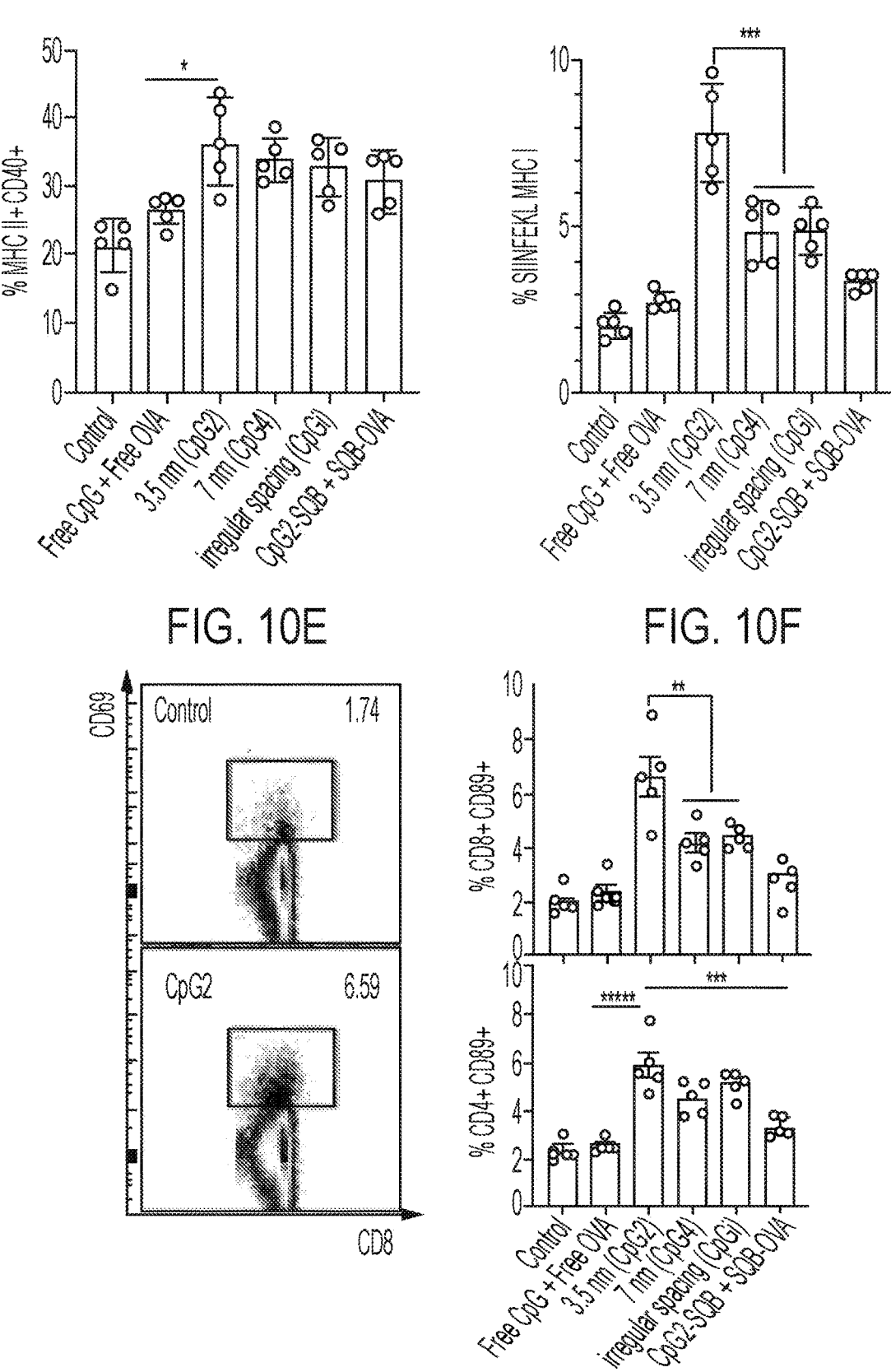
Figure 10H:
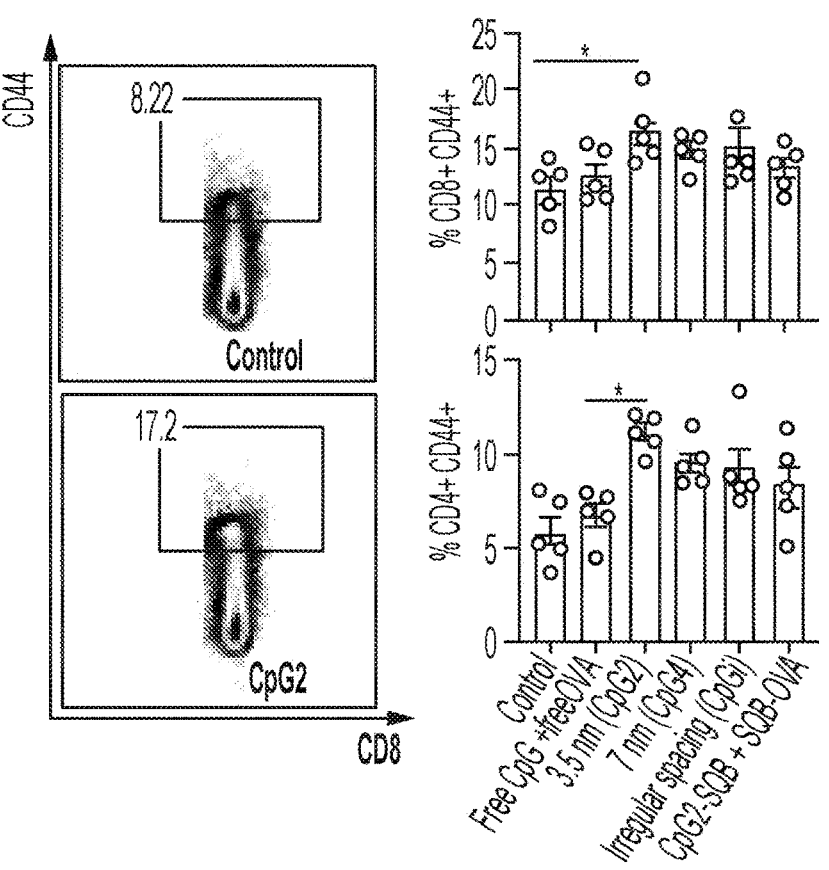
Figures 10I, 10J:
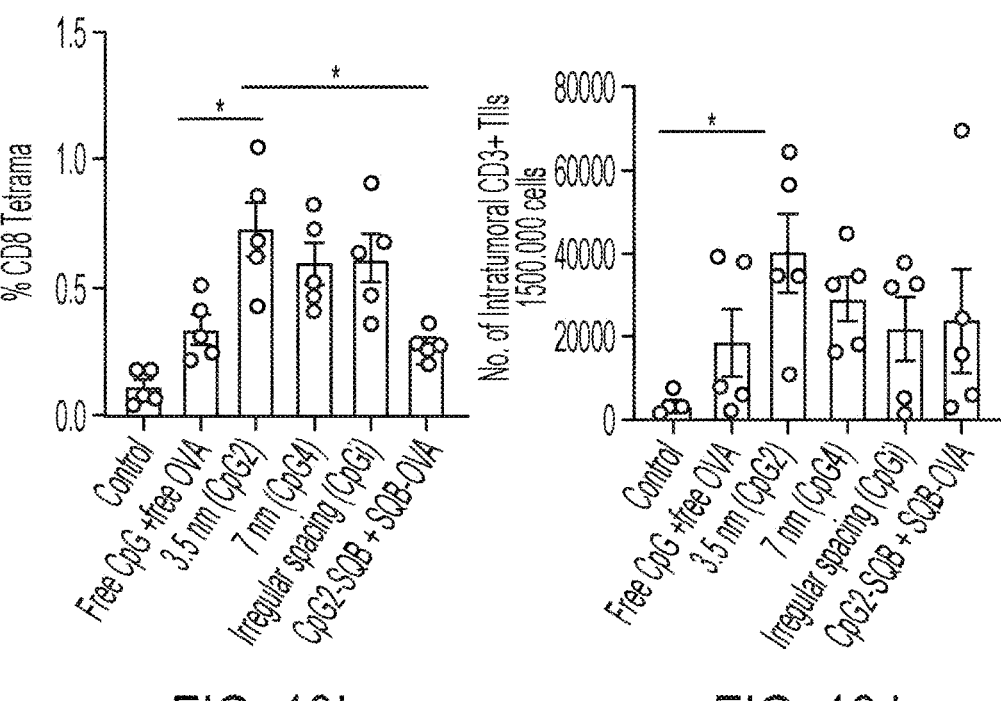

After the tumor mice were given three treatments of vaccine, the mice were sacrificed, and the lymph nodes and tumor tissues were processed to single cell suspension for flow cytometry. In the lymph node, more CD11c+ DC cells were found in the CpG2 group (FIGS. 10A, 10C). There were also more CD11c+ in group of CpG an OVA delivered separately on SQB (FIG. 10C), however, this did not correlated to DC and T cell activation which proved the importance of co-delivery. Treg cells were proved high in vivo again when free CpG and free OVA were applied (FIGS. 10B, 10D). MHC II and CD40 double positive mature DCs significantly increased in CpG2 group (FIG. 10E). SIINFEKL MHCI+expression was remarkably increased in CpG2 compared to other spacing strategy (FIG. 10F). CD8 and CD4 T cells were activated the most in CpG2 group indicated by CD69 expression and memory marker CD44 (FIGS. 10G, 10H). CD8 OVA tetramer cells increased about 7 times in the lymph node in CpG2 group (FIG. 10I). In the tumor tissue, massive infiltrated CD3+ T cells accumulated in CpG2 vaccine applied group (FIG. 10J). Among the infiltrated CD8 T cells, a majority of them (around 40%) are OVA-specific CD8 T cells in CpG2 applied group, significantly more than CpG4 spacing at 7 nm (FIG. 10K). More IL-2+ CD8 T cells could be found in CpG2 group as well (FIG. 10L). The Gr-1+CD11b+ myeloid derived suppressive cells were found not increased in origami vaccine applied groups (FIG. 10M). These results indicated CpG spacing at 3.5 nm on SQB improved Th1 immune response in the treated tumor through a cohort of immune cell activation.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A nucleic acid nanostructure conjugated to an antigen, oligolysine-polyethylene glycol copolymer, and CpG ligand, wherein the distance between any two adjacent molecules of CpG is 2 nm to 10 nm and/or the density of CpG ligand on the nucleic acid nanostructure is 1 molecule of CpG ligand per 5 to 50 nm$^2$.

2. The nucleic acid nanostructure of claim 1, wherein the distance between any two adjacent molecules of CpG is 2 nm to 10 nm.

3. The nucleic acid nanostructure of claim 2, wherein the distance between any two adjacent molecules of CpG is 2-3 nm, 3-4 nm, 4-6 nm, or 6-8 nm, optionally 2.5 nm, 3.5 nm, 5 nm, or 7 nm.

4. The nucleic acid nanostructure of claim 1, wherein the density of CpG ligand on the nucleic acid nanostructure is 1 molecule of CpG ligand per 5 to 50 nm$^2$.

5. The nucleic acid nanostructure of claim 3, wherein the distance between any two adjacent molecules of CpG is 3.5 nm.

6. The nucleic acid nanostructure of claim 1, wherein the nucleic acid nanostructure comprises a square-lattice structure.

7. The nucleic acid nanostructure of claim 6, wherein the CpG ligand is located on at least one surface of the nucleic acid nanostructure.

8. The nucleic acid nanostructure of claim 6, wherein the antigen is located on at least one surface of the nucleic acid nanostructure.

9. The nucleic acid nanostructure of claim 7, wherein the CpG ligand and the antigen are located on different surfaces of the nucleic acid nanostructure, relative to each other.

10. The nucleic acid nanostructure of claim 1, wherein the nucleic acid nanostructure comprises 5 to 25, 10 to 25, or 15 to 25 CpG ligand molecules.

11. The nucleic acid nanostructure of claim 1, wherein the CpG ligand and/or antigen are located on a single surface of the nucleic acid nanostructure.

12. The nucleic acid nanostructure of claim 1, wherein the oligolysine-polyethylene glycol (PEG) copolymer comprises ten lysine residues and a PEG 5K moiety ($K_{10}PEG_{5k}$).

13. The nucleic acid nanostructure of claim 1, wherein the antigen and/or the oligolysine-PEG copolymer is covalently conjugated to the nanostructure.

14. The nucleic acid nanostructure of claim 1, wherein the oligolysine-PEG copolymer is covalently conjugated to the nanostructure.

15. The nucleic acid nanostructure of claim 1, wherein the nucleic acid of the nanostructure comprises DNA, RNA, or a mixture of DNA and RNA.

16. A DNA nanostructure conjugated to an antigen, oligolysine-polyethylene glycol copolymer, and CpG ligand, wherein the DNA nanostructure comprises a square-lattice structure, the CpG ligand is uniformly spaced with a density of 1 molecule of CpG ligand per 10-30 nm$^2$, and the distance between any two adjacent molecules of CpG is 3-5 nm.

17. A method of treating a tumor comprising administering to a subject in need thereof the nanostructure of claim 1 in an effective amount to produce a CD8+ T cell immune response to the antigen in the subject.

18. The method of claim 17, wherein the antigen is a tumor antigen.

19. The method of claim 17, wherein the effective amount is sufficient to:

(a) reduce tumor volume by at least 2-fold;

(b) stimulate cytokine production in dendritic cells of the subject, wherein the cytokine production is at least 10% higher than cytokine production by dendritic cells in a subject administered antigen only or antigen and free CpG oligonucleotides, optionally wherein the cytokine is Interleukin-10 (IL10) and/or IL12;

(c) increase antigen uptake in dendritic cells of the subject, wherein the antigen uptake is at least 10% higher than antigen uptake by dendritic cells in a subject administered antigen only or antigen and free CpG oligonucleotides;

(d) stimulates a stronger Th1 immune response, relative to stimulation of a Th2 response;

(e) stimulates CD8+ T cell proliferation by at least 10%, at least 15%, or at least 20% relative to CD8+ T cell proliferation in control cells in a subject administered antigen only or antigen and free CpG oligonucleotides; and/or (f) stimulates IFN-γ expression in OT-I CD8+ T cells of the subject, wherein the IFN-γ expression is at least 10%, at least 15%, or at least 20% higher than IFN-γ expression by in OT-I CD8+ T cells in a subject administered antigen only or antigen and free CpG oligonucleotides.

*    *    *    *    *

```
                         SEQUENCE LISTING

<160> NUMBER OF SEQ ID NOS: 13

<210> SEQ ID NO 1
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 1

Ser Ile Ile Asn Phe Glu Lys Leu
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(5)
<223> OTHER INFORMATION: Lysine may be modified by a functional group
<220> FEATURE:
<221> NAME/KEY: SITE
<222> LOCATION: (2)..(2)
<223> OTHER INFORMATION: Xaa may be any non-lysine amino acid or Xaa may
      be absent
<220> FEATURE:
<221> NAME/KEY: REPEAT
<222> LOCATION: (3)..(4)
<220> FEATURE:
<221> NAME/KEY: SITE
<222> LOCATION: (4)..(4)
<223> OTHER INFORMATION: Xaa may be any non-lysine amino acid or Xaa may
      be absent

<400> SEQUENCE: 2

Lys Xaa Lys Xaa Lys
1               5

<210> SEQ ID NO 3
<211> LENGTH: 3
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(1)
<223> OTHER INFORMATION: Xaa may be any non-lysine amino acid or Xaa may
      be absent
```

```
<220> FEATURE:
<221> NAME/KEY: SITE
<222> LOCATION: (1)..(3)
<223> OTHER INFORMATION: Lys may be modified by a functional group
<220> FEATURE:
<221> NAME/KEY: REPEAT
<222> LOCATION: (2)..(3)
<220> FEATURE:
<221> NAME/KEY: SITE
<222> LOCATION: (3)..(3)
<223> OTHER INFORMATION: Xaa may be any non-lysine amino acid or Xaa may
     be absent

<400> SEQUENCE: 3

Xaa Lys Xaa
1

<210> SEQ ID NO 4
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(4)
<223> OTHER INFORMATION: Lys may be modified by a functional group
<220> FEATURE:
<221> NAME/KEY: SITE
<222> LOCATION: (2)..(2)
<223> OTHER INFORMATION: Xaa may be any non-lysine amino acid or may be
     absent
<220> FEATURE:
<221> NAME/KEY: REPEAT
<222> LOCATION: (3)..(4)
<220> FEATURE:
<221> NAME/KEY: SITE
<222> LOCATION: (4)..(4)
<223> OTHER INFORMATION: Xaa may be any non-lysine amino acid or may be
     absent

<400> SEQUENCE: 4

Lys Xaa Lys Xaa
1

<210> SEQ ID NO 5
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(4)
<223> OTHER INFORMATION: Lys may be modified by a functional group
<220> FEATURE:
<221> NAME/KEY: SITE
<222> LOCATION: (1)..(1)
<223> OTHER INFORMATION: Xaa may be any non-lysine amino acid or may be
     absent
<220> FEATURE:
<221> NAME/KEY: REPEAT
<222> LOCATION: (2)..(3)
<220> FEATURE:
<221> NAME/KEY: SITE
<222> LOCATION: (3)..(3)
<223> OTHER INFORMATION: Xaa may be any non-lysine amino acid or may be
     absent

<400> SEQUENCE: 5

Xaa Lys Xaa Lys
1
```

-continued

```
<210> SEQ ID NO 6
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(7)
<223> OTHER INFORMATION: Lys may be modified by a functional group
<220> FEATURE:
<221> NAME/KEY: SITE
<222> LOCATION: (2)..(3)
<223> OTHER INFORMATION: Xaa may be any non-lysine amino acid or may be
      absent
<220> FEATURE:
<221> NAME/KEY: REPEAT
<222> LOCATION: (4)..(6)
<220> FEATURE:
<221> NAME/KEY: SITE
<222> LOCATION: (5)..(6)
<223> OTHER INFORMATION: Xaa may be any non-lysine amino acid or may be
      absent

<400> SEQUENCE: 6

Lys Xaa Xaa Lys Xaa Xaa Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(5)
<223> OTHER INFORMATION: Lys may be modified by a functional group
<220> FEATURE:
<221> NAME/KEY: SITE
<222> LOCATION: (1)..(2)
<223> OTHER INFORMATION: Xaa may be any non-lysine amino acid or may be
      absent
<220> FEATURE:
<221> NAME/KEY: REPEAT
<222> LOCATION: (3)..(5)
<220> FEATURE:
<221> NAME/KEY: SITE
<222> LOCATION: (4)..(5)
<223> OTHER INFORMATION: Xaa may be any non-lysine amino acid or may be
      absent

<400> SEQUENCE: 7

Xaa Xaa Lys Xaa Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(6)
<223> OTHER INFORMATION: Lys may be modified by a functional group
<220> FEATURE:
<221> NAME/KEY: SITE
<222> LOCATION: (2)..(3)
<223> OTHER INFORMATION: Xaa may be any non-lysine amino acid or may be
      absent
<220> FEATURE:
<221> NAME/KEY: REPEAT
<222> LOCATION: (4)..(6)
<220> FEATURE:
```

```
<221> NAME/KEY: SITE
<222> LOCATION: (5)..(6)
<223> OTHER INFORMATION: Xaa may be any non-lysine amino acid or may be
      absent

<400> SEQUENCE: 8

Lys Xaa Xaa Lys Xaa Xaa
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(6)
<223> OTHER INFORMATION: Lys may be modified by a functional group
<220> FEATURE:
<221> NAME/KEY: SITE
<222> LOCATION: (1)..(2)
<223> OTHER INFORMATION: Xaa may be any non-lysine amino acid or may be
      absent
<220> FEATURE:
<221> NAME/KEY: REPEAT
<222> LOCATION: (3)..(5)
<220> FEATURE:
<221> NAME/KEY: SITE
<222> LOCATION: (4)..(5)
<223> OTHER INFORMATION: Xaa may be any non-lysine amino acid or may be
      absent

<400> SEQUENCE: 9

Xaa Xaa Lys Xaa Xaa Lys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(9)
<223> OTHER INFORMATION: Lys may be modified by a functional group
<220> FEATURE:
<221> NAME/KEY: SITE
<222> LOCATION: (2)..(4)
<223> OTHER INFORMATION: Xaa may be any non-lysine amino acid or may be
      absent
<220> FEATURE:
<221> NAME/KEY: REPEAT
<222> LOCATION: (5)..(8)
<223> OTHER INFORMATION: Xaa may be any non-lysine amino acid or may be
      absent
<220> FEATURE:
<221> NAME/KEY: SITE
<222> LOCATION: (6)..(8)
<223> OTHER INFORMATION: Xaa may be any non-lysine amino acid or may be
      absent

<400> SEQUENCE: 10

Lys Xaa Xaa Xaa Lys Xaa Xaa Xaa Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic polypeptide
```

-continued

```
<220> FEATURE:
<221> NAME/KEY: SITE
<222> LOCATION: (1)..(7)
<223> OTHER INFORMATION: Lys may be modified by a functional group
<220> FEATURE:
<221> NAME/KEY: SITE
<222> LOCATION: (1)..(3)
<223> OTHER INFORMATION: Xaa may be any non-lysine amino acid or may be
      absent
<220> FEATURE:
<221> NAME/KEY: REPEAT
<222> LOCATION: (4)..(7)
<220> FEATURE:
<221> NAME/KEY: SITE
<222> LOCATION: (5)..(7)
<223> OTHER INFORMATION: Xaa may be any non-lysine amino acid or may be
      absent

<400> SEQUENCE: 11

Xaa Xaa Xaa Lys Xaa Xaa Xaa
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(8)
<223> OTHER INFORMATION: Lys may be modified by a functional group
<220> FEATURE:
<221> NAME/KEY: SITE
<222> LOCATION: (2)..(4)
<223> OTHER INFORMATION: Xaa may be any non-lysine amino acid or may be
      absent
<220> FEATURE:
<221> NAME/KEY: REPEAT
<222> LOCATION: (5)..(8)
<220> FEATURE:
<221> NAME/KEY: SITE
<222> LOCATION: (6)..(8)
<223> OTHER INFORMATION: Xaa may be any non-lysine amino acid or may be
      absent

<400> SEQUENCE: 12

Lys Xaa Xaa Xaa Lys Xaa Xaa Xaa
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(8)
<223> OTHER INFORMATION: Lys may be modified by a functional group
<220> FEATURE:
<221> NAME/KEY: SITE
<222> LOCATION: (1)..(3)
<223> OTHER INFORMATION: Xaa may be any non-lysine amino acid or may be
      absent
<220> FEATURE:
<221> NAME/KEY: REPEAT
<222> LOCATION: (4)..(7)
<220> FEATURE:
<221> NAME/KEY: SITE
<222> LOCATION: (5)..(7)
<223> OTHER INFORMATION: Xaa may be any non-lysine amino acid or may be
      absent
```

-continued

<400> SEQUENCE: 13

Xaa Xaa Xaa Lys Xaa Xaa Xaa Lys
1               5